United States Patent
Dadgar et al.

(10) Patent No.: US 12,018,240 B2
(45) Date of Patent: Jun. 25, 2024

(54) HIGH-THROUGHPUT MICROFLUIDIC CHIP HAVING PARALLELIZED CONSTRICTIONS FOR PERTURBING CELL MEMBRANES

(71) Applicant: STEMCELL TECHNOLOGIES CANADA INC., Vancouver (CA)

(72) Inventors: Maisam Dadgar, Cambridge, MA (US); Jacquelyn L. Sikora Hanson, Watertown, MA (US); Armon R. Sharei, Somerville, MA (US)

(73) Assignee: STEMCELL TECHNOLOGIES CANADA INC., Vancouver (CA)

( * ) Notice: Subject to any disclaimer, the term of this patent is extended or adjusted under 35 U.S.C. 154(b) by 19 days.

(21) Appl. No.: 17/562,815

(22) Filed: Dec. 27, 2021

(65) Prior Publication Data

US 2022/0204902 A1    Jun. 30, 2022

Related U.S. Application Data

(60) Provisional application No. 63/131,430, filed on Dec. 29, 2020.

(51) Int. Cl.
*G01N 33/68* (2006.01)
*B01L 3/00* (2006.01)
(Continued)

(52) U.S. Cl.
CPC ....... *C12M 23/16* (2013.01); *B01L 3/502707* (2013.01); *C12M 33/12* (2013.01); *B01L 2200/12* (2013.01); *B01L 2300/0819* (2013.01)

(58) Field of Classification Search
CPC ...... C12M 23/16; C12M 33/12; C12M 35/04; B01L 3/502707; B01L 2200/12;
(Continued)

(56) References Cited

U.S. PATENT DOCUMENTS

2014/0287509 A1*  9/2014  Sharei ................ C12N 5/0602
                                                         435/375

FOREIGN PATENT DOCUMENTS

WO    2013059343 A1    4/2013
WO    2015023982 A1    2/2015
(Continued)

OTHER PUBLICATIONS

Sharei, Armon, et al. "A vector-free microfluidic platform for intracellular delivery." Proceedings of the National Academy of Sciences 110.6 (2013): 2082-2087. (Year: 2013).*

*Primary Examiner* — Jennifer Wecker
*Assistant Examiner* — Oyeleye Alexander Alabi
(74) *Attorney, Agent, or Firm* — BERESKIN & PARR LLP/S.E.N.C.R.L., s.r.l.; Micheline Gravelle

(57) ABSTRACT

A microfluidic chip for causing the delivery of a payload to a cell comprises a plurality of constrictions configured to allow a cell suspension to flow through one or more of the plurality of constrictions from a first fluid flow region to a second fluid flow region within the microfluidic chip, wherein a cross-sectional width of each of the plurality of constrictions is less than a diameter of cells in the cell suspension, such that membranes of the cells are perturbed when passing through the constrictions such that a payload is able to pass through the perturbed cell membranes, and wherein a quotient of a cross-sectional area over a cross-sectional perimeter of each of the plurality of constrictions is greater than greater than or equal to 0.5 µm.

27 Claims, 37 Drawing Sheets
(3 of 37 Drawing Sheet(s) Filed in Color)

(51) Int. Cl.
*C07C 309/65* (2006.01)
*C07C 309/73* (2006.01)
*C12M 1/26* (2006.01)
*C12M 3/06* (2006.01)
*G01N 21/33* (2006.01)
*G01N 21/64* (2006.01)
*G01N 33/52* (2006.01)

(58) Field of Classification Search
CPC ..... B01L 2300/0819; B01L 2200/0663; B01L 2400/0487; B01L 2400/086; B01L 3/502761; B01L 3/502746
See application file for complete search history.

(56) References Cited

FOREIGN PATENT DOCUMENTS

| | | |
|---|---|---|
| WO | 2016070136 A1 | 5/2016 |
| WO | 2016077761 A1 | 5/2016 |
| WO | 2016115179 A1 | 7/2016 |
| WO | 2017192785 A1 | 11/2017 |
| WO | 2019126212 A1 | 6/2019 |
| WO | 2020015098 A1 | 1/2020 |

\* cited by examiner

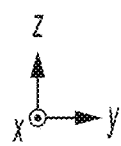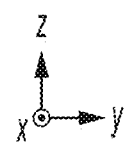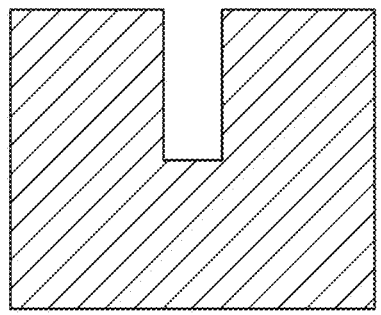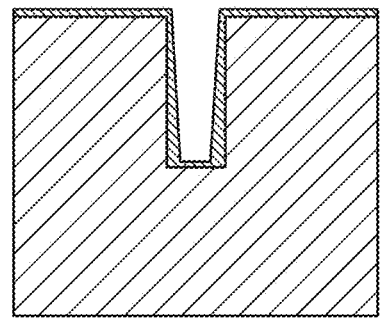
FIG. 2A        FIG. 2B

HIGH-THROUGHPUT MICROFLUIDIC CHIP HAVING PARALLELIZED CONSTRICTIONS FOR PERTURBING CELL MEMBRANES

CROSS-REFERENCE TO RELATED APPLICATION(S)

This application claims benefit claims the benefit of U.S. Provisional Application No. 63/131,430, filed Dec. 29, 2020, the entire contents of which are hereby incorporated herein by reference.

FIELD

The present disclosure relates to delivery of a payloads into cells, and more specifically to microfluidic constricting channels that may perturb cell membranes to allow the passage of payloads through the perturbed membranes.

BACKGROUND

The controlled delivery of various materials into cells is important in the developing medical field of cell therapy. For example, various research and therapeutic applications may include the delivery of peptides, nucleic acids, proteins, small molecules, and nanomaterials through cell membranes and into cells. As discussed in WO2013059343, WO2015023982, PCT/US2015/058489, PCT/US2015/060689, and PCT/US2016/13113, constricting microfluidic channels may be used to deliver compounds and other payloads into cells. As disclosed in PCT/US2018/66295, tabletop laboratory and/or clinical systems may be configured to force a cell suspension through one or more constrictions of a microfluidic chip having constricting channels or constricting pores, in order to cause perturbations in the membranes of the cells in the cell suspension.

SUMMARY OF THE INVENTION

As explained above, systems for intracellular payload delivery include systems configured to force cells through one or more constricting channels or constricting pores in order to cause perturbations in the membranes of the cells in a cell suspension when the cell suspension flows through the constriction cartridge. However, known systems for intracellular payload delivery are prone to clogging of constrictions, have insufficient throughput rates, and are not sufficiently simple and efficient to fabricate.

Accordingly, there is a need for improved systems, methods, and techniques for intracellular payload delivery, including a need for improved microfluidic cell-constricting chips having high throughput rates and low clogging rates. There is a need microfluidic cell-constricting chips having improved geometric configurations, improved throughput, improved resistance to clogging or other failure, and/or improved ease and efficiency of manufacture. The systems, methods, and techniques disclosed herein may address one or more of these needs to improve the geometric configurations, throughput, resistance to clogging or other failure, ease and efficiency of manufacture, and capacity of microfluidic cell-constricting chips and/or systems, methods of use, and/or methods of manufacture.

Disclosed herein are high-throughput microfluidic chips for use in systems for delivering a payload to a cell in a cell suspension. The chips comprise a plurality of parallelized constrictions (e.g., constricting channels) through which a cell suspension may be forced under pressure. The cells of the cell suspension may be deformed and their membranes perturbed due to passage through a cell-deforming constriction of the microfluidic chip. As explained herein, throughput and clogging properties of the chip may be improved due to several characteristics of the chips disclosed herein.

First, the chips disclosed herein may include a large number of parallelized constrictions dividing a first fluid flow region from a second fluid flow region. For example, chips such as those disclosed herein may have hundreds or thousands of parallelized microfluidic constrictions. When cell suspension fluid in the first fluid flow region is pressurized, it may be able to flow through any one of the constrictions into the second fluid flow region, increasing throughput over chips having fewer constrictions.

Second, the chips disclosed herein may have one or more constrictions for which the quotient of cross-sectional area over the cross-sectional perimeter is higher than in previously known designs. In some embodiments, increasing this quotient may be achieved by etching deep, narrow, rectangular constrictions (e.g., slit-shaped constrictions) into a substrate (e.g., a silicon substrate). The constrictions may be formed by etching sufficiently deeply while maintaining constriction side walls within a sufficient angular threshold of parallel to one another. Furthermore, the constrictions may be formed by etching sufficiently deeply while maintaining the side walls within a predefined envelope (e.g., tolerance) of distance from one another, such that a cell forced through the constriction may be deformed by the side walls regardless of the location (e.g., the etch depth) at which the cell passes through the constriction. In this way, each deep, narrow, rectangular constriction may have an increased individual throughput, due to a larger cross-sectional constriction area, as compared to constrictions that have widths configured for cells of the same size, but that are not etched as deeply into a substrate. Furthermore, because clogging of constrictions may be prone to be caused by the edges and corners of the constrictions, deep, narrow, rectangular constrictions may clog at a decreased rate as compared to constrictions that have widths configured for cells of the same size, but that are not etched as deeply into a substrate. In some embodiments, thus, increasing cross-sectional constriction area while minimizing cross-sectional constriction perimeter may increase per-constriction throughput while minimizing likelihood and/or extent of constriction clogging.

Third, the chips disclosed herein may have geometries configured to ensure sufficiently uniform flow velocity and flow patterns as the cell suspension approaches and flows through the plurality of constrictions. In some embodiments, the plurality of constrictions may be arranged in a line forming a barrier or wall between a first flow region upstream of the parallelized plurality of constrictions and a second flow region downstream of the parallelized plurality of constrictions. The barrier formed by the plurality of constrictions may be located at a sufficient distance from an inlet port of the chip and a length of the barrier may be sufficiently short in relation to said distance that the flow velocity and flow patters through the plurality of constrictions are sufficiently uniform to maintain high throughput and low clogging.

Fourth, the constrictions disclosed herein may have geometries configured to ensure sufficiently uniform flow patterns in and around the constriction and to ensure sufficiently high flow velocities and throughput flow rates through the constrictions. In some embodiments, the constrictions have an approach region through which fluid flows as it approaches the narrowest point of the constriction. The approach region can be defined by one or more tapered walls, such as a tapered side wall that tapers toward the narrowest point in the constriction at a predefined angle. The predefined angle may be set, in conjunction with the width of the narrowest point of the constriction and other properties of the chip and cell suspension, to ensure uniform flow patterns and sufficient flow velocities and throughputs.

In some embodiments, a first microfluidic chip for causing the delivery of a payload to a cell is provided, the first chip comprising: a fluid inlet configured to receive flow of a cell suspension and pass the cell suspension to a first fluid flow region within the microfluidic chip; a plurality of constrictions fluidly connected to the first fluid flow region to allow the cell suspension to flow through one or more of the plurality of constrictions from the first fluid flow region to a second fluid flow region within the microfluidic chip, wherein: a cross-sectional width of each of the plurality of constrictions is less than a diameter of cells in the cell suspension, such that membranes of the cells are perturbed when passing through the constrictions such that a payload is able to pass through the perturbed cell membranes; and a quotient of a cross-sectional area over a cross-sectional perimeter of each of the plurality of constrictions is greater than greater than or equal to 0.5 µm.

In some embodiments, a first method of causing delivery of a payload to a cell is provided, the first method comprising: receiving flow of a cell suspension into a first fluid flow region of a microfluidic chip, the cell suspension comprising a plurality of cells; and causing the cell suspension to flow from the first fluid flow region through a plurality of constrictions of the microfluidic chip, wherein: a cross-sectional width of each of the plurality of constrictions is less than a diameter of cells in the cell suspension, such that membranes of the cells are deformed when passing through the constrictions such that a payload is able to pass through the deformed cell membranes; and a quotient of a cross-sectional area over a cross-sectional perimeter of each of the plurality of constrictions is greater than greater than or equal to 0.5 µm.

In some embodiments, a second method of fabricating a microfluidic chip for causing the delivery of a payload to cells is provided, the second method comprising: etching into a substrate to form a first fluid flow region configured to allow a cell suspension to flow from an inlet port through the first fluid flow region; and etching into the substrate to form a plurality of constrictions configured to allow flow of the cell suspension from the first fluid flow region through the constrictions, wherein: a cross-sectional width of each of the plurality of constrictions is less than a diameter of cells in the cell suspension, such that membranes of the cells are deformed when passing through the constrictions such that a payload is able to pass through the deformed cell membranes; and a quotient of a cross-sectional area over a cross-sectional perimeter of each of the plurality of constrictions is greater than greater than or equal to 0.5 µm.

In some embodiments, a second microfluidic chip for causing the delivery of a payload to a cell is provided, the second chip comprising: a fluid inlet configured to receive flow of a cell suspension and pass the cell suspension to a first fluid flow region within the microfluidic chip; a first plurality of constrictions fluidly connected to the first fluid flow region to allow the cell suspension to flow through one or more of the first plurality of constrictions from the first fluid flow region to a second fluid flow region within the microfluidic chip; and a second plurality of constrictions fluidly connected to the second fluid flow region to allow the cell suspension to flow through one or more of the second plurality of constrictions from the second fluid flow region to a third fluid flow region within the microfluidic chip, wherein: a cross-sectional width of each of the constrictions of the first plurality of constrictions and the second plurality of constrictions is less than a diameter of cells in the cell suspension, such that membranes of the cells are perturbed when passing through the constrictions such that a payload is able to pass through the perturbed cell membranes; and a quotient of a cross-sectional area over a cross-sectional perimeter of each of the constrictions of the first plurality of constrictions and the second plurality of constrictions is greater than greater than or equal to 0.5 µm.

In some embodiments, any one or more of the features, characteristics, or elements discussed above with respect to any of the embodiments may be incorporated into any of the other embodiments mentioned above or described elsewhere herein. In some embodiments, any one or more of the features, characteristics, or elements discussed elsewhere in this disclosure may be incorporated into any one or more of the embodiments mentioned above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A illustrates an overhead view of the chip and a magnified highlight of constrictions of the chip, in accordance with some embodiments; FIG. 1B illustrates an overhead view of constrictions and guide channels of the chip, in accordance with some embodiments; FIG. 1C illustrates a cross-sectional view of constrictions of the chip, in accordance with some embodiments.

FIGS. 2A-2B illustrate steps of fabrication of chip for delivering a payload to a cell, in accordance with some embodiments. FIG. 2A illustrates a constriction following an etching step, in accordance with some embodiments; FIG. 2B illustrates the constriction following a deposition step, in accordance with some embodiments.

DETAILED DESCRIPTION OF THE INVENTION

Figure 1A:
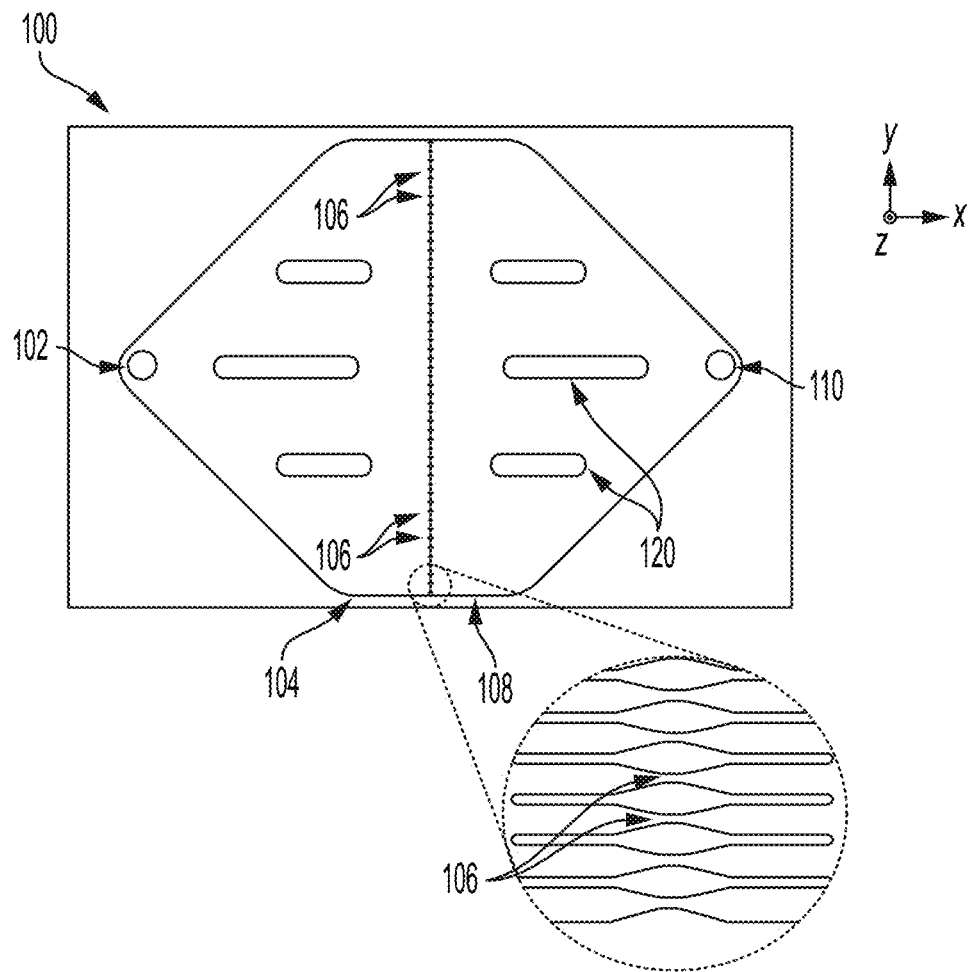
FIGS. 1A-1C illustrate various views of a chip for delivering a payload to a cell, in accordance with some embodiments.

Disclosed below are high-throughput microfluidic chips for use in systems for delivering a payload to a cell in a cell suspension. The chips comprise a plurality of parallelized constrictions (e.g., constricting channels) through which a cell suspension may be forced under pressure. The cells of the cell suspension may be deformed and their membranes perturbed due to passage through a cell-deforming constriction of the microfluidic chip. As explained herein, throughput and clogging properties of the chip may be improved due to several characteristics of the chips disclosed herein.

Below, the description of FIGS. 1A-1C describe an exemplary embodiment of a microfluidic chip having parallelized constrictions for intracellular payload delivery. The description of FIGS. 2A-2B then describe fabrication of a constriction in a microfluidic chip for intracellular payload delivery. The description of FIGS. 3A-3C, 4, 5A-5C, and 6A-6C then describe various geometries for approach regions adjacent to constrictions of a chip for intracellular payload delivery. The description of FIG. 7 then describes an exemplary embodiment of a microfluidic chip having multiple sets of parallelized constrictions and wherein the sets are in series with one another. The description of FIG. 8 then describes a method of use of chips such as those disclosed herein. As described below, the chips and/or chip geometries described with reference to FIGS. 1-7 may, in some embodiments, be used in method 800. The description of FIG. 9 then describes a cartridge holding chips for delivering a payload to a cell, in accordance with some embodiments. The description of FIGS. 10A-10C then describe chips having fluid flow regions having various geometries. The description of FIGS. 11, 12, and 13A-13O then pertain to experimental data from several examples described herein.

The following description sets forth exemplary systems, methods, techniques, parameters, and the like. It should be recognized, however, that such description is not intended as a limitation on the scope of the present disclosure but is instead provided as a description of exemplary embodiments.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

It is further understood that the terms "includes," "including," "comprises," and/or "comprising," specify the presence of stated features, integers, steps, operations, elements, and/or components, but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The term "about" as used herein refers to the usual error range for the respective value readily known to the skilled person in this technical field. Reference to "about" a value or parameter herein includes (and describes) embodiments that are directed to that value or parameter per se.

Although the description herein uses terms first, second, etc. to describe various elements, these elements should not be limited by the terms. These terms are only used to distinguish one element from another.

For any of the structural and functional characteristics described herein, methods of determining these characteristics are known in the art.

All references cited herein, including patent applications and publications, are incorporated by reference in their entirety.

Microfluidic Chip Geometries for Intracellular Payload Delivery

Described below are microfluidic chips for increased throughput and decreased cell clogging.

Figure 1B:
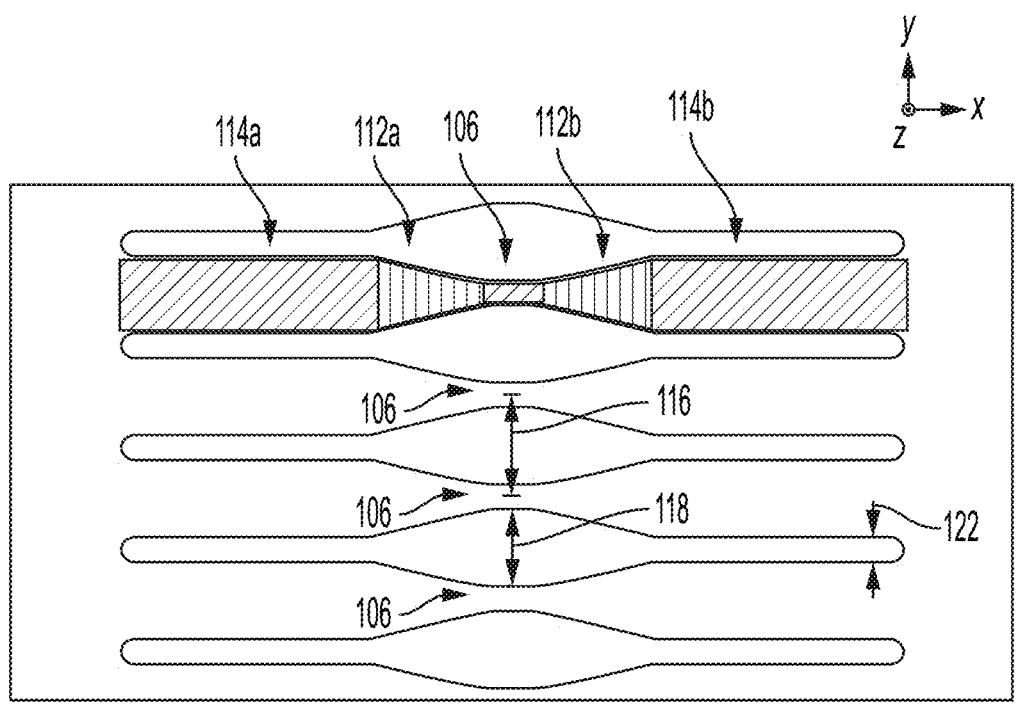
Figure 1C:
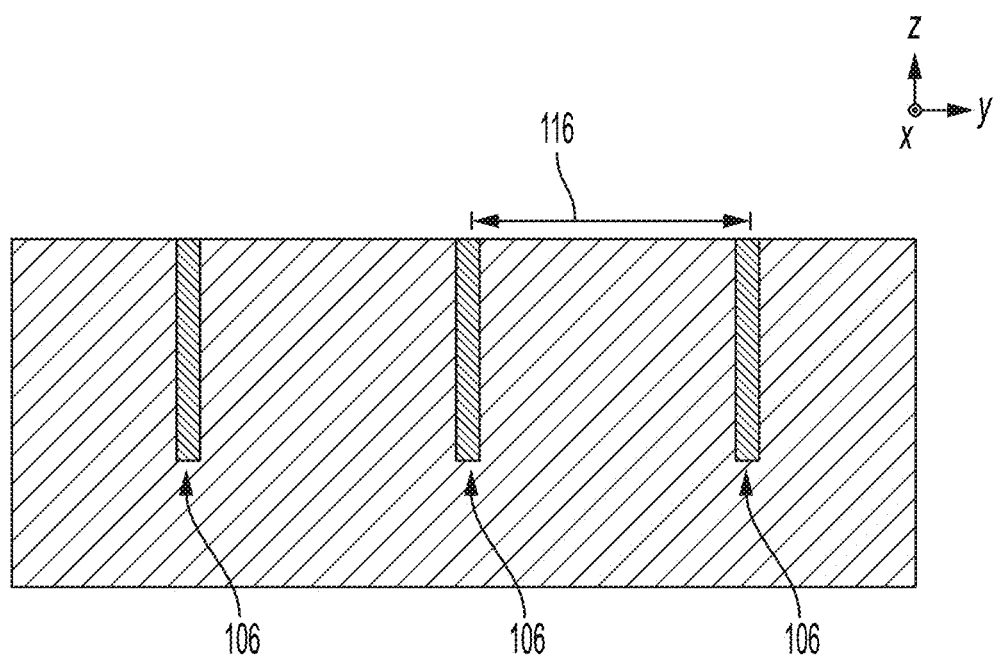

FIGS. 1A-1C illustrate various views of a chip 100 for delivering a payload to a cell, in accordance with some embodiments. FIG. 1A illustrates an overhead view of chip 100 and a magnified highlight of constrictions of the chip, in accordance with some embodiments; FIG. 1B illustrates an overhead view of constrictions and guide channels of chip 100, in accordance with some embodiments; FIG. 1C illustrates a cross-sectional view of constrictions of chip 100, in accordance with some embodiments.

Microfluidic chip 100 is configured to receive a flow of a fluid at fluid inlet 110. The fluid may comprise a cell suspension. In some embodiments, the fluid may comprise a payload for delivery into a cell, wherein the payload may comprise any suitable cargo for delivery into a cell.

For purposes of the description herein, the directions and dimensions of chip 100 may be referred to by the following convention: the x-direction or x-dimension may refer to the dimension running horizontally in FIG. 1A (the x-direction is the direction of overall flow of fluid through chip 100 from a flow inlet to a flow outlet); the y-direction or y-dimension may refer to the dimension running vertically in FIG. 1A; and the z-direction or z-dimension may refer to the dimension running in and out of the page in FIG. 1A.

In some embodiments, chip 100 may be a microfluidic chip configured to guide the flow of fluid through one or more constrictions (e.g., constricting channels) that are sufficiently narrow in at least one dimension to deform cells that are forced through the constrictions under pressure. Deformation of the cells as they pass through a constriction under pressure may cause perturbation of the cell membranes such that a payload suspended in the cell suspension (either by being suspended in the suspension before passage through the constriction(s) or added to the suspension afterwards) may pass through the perturbed cell membrane to enter a cell.

In the example of chip 100, fluid (e.g., a cell suspension) flowing through chip 100 may flow into chip 100 via inlet port 102 and may flow from inlet 102 into first fluid flow region 104. From first fluid flow region 104, the fluid may flow (e.g., by being forced under pressure) through a plurality of parallelized constrictions 106 and into second fluid flow region 108. The fluid may then flow from second fluid flow region 108 out of chip 100 via outlet port 110. A distance between fluid inlet port 102 and fluid outlet port 110 can extend in a direction perpendicular to a planar surface (e.g., inner surface) of a substrate of chip 100. A distance between fluid inlet port 102 and fluid outlet port 110 may be 5-30 mm, 8-25 mm, or 10-20 mm. In some embodiments, the distance between fluid inlet port 102 and fluid outlet port 110 may be less than or equal to 450 mm, 250 mm, 100 mm, 50 mm, 30 mm, 25 mm, 20 mm, 15 mm, 10 mm, or 8 mm. In some embodiments, the distance between fluid inlet port 102 and fluid outlet port 110 may be greater than or equal to 5 mm, 8 mm, 10 mm, 15 mm, 20 mm, 25 mm, 30 mm, 50 mm, 100 mm, 250 mm, or 450 mm. In some embodiments, between fluid inlet port 102 and fluid outlet port 110 of microfluidic chip 100 may be interchangeable.

In some embodiments, first fluid flow region 104, constrictions 106, and second fluid flow region 108 may all be formed as recessed space formed within a substrate, such as a silicon substrate. In some embodiments, etching may be performed in the z-direction by etching down into a top surface of the substrate. In some embodiments, wet or dry etching may be used. In some embodiments, deep reactive ion etching (DRIE) may be used. After etching into the substrate to define the recessed space forming first fluid flow region 104, constrictions 106, and/or second fluid flow region 108, a top layer may be affixed atop the substrate layer to enclose regions 104 and 108 and constrictions 106 in the z-direction.

In some embodiments, inlet port 102 and/or outlet port 110 may be formed as openings in the top layer; in some embodiments, inlet port 102 and/or outlet port 110 may be formed as openings in the etched substrate layer, such as openings through a bottom of the substrate layer in the z-direction or as openings through a side of the substrate in the x-direction and/or y-direction.

In some embodiments, chip 100 may include pillars 120, which may extend through first fluid flow region 104 and/or second fluid flow region 108. Pillars 120 may serve as support structures that hold up a top layer of chip 100 and/or to which a top layer of chip 100 may be bonded. In some embodiments, the shape and/or placement of pillars 120 may be selected so as to minimize disruption of uniform flow patterns and flow velocity to all portions of the boundary formed by constrictions 106 between first fluid flow region 104 and second fluid flow region 108; for example, pillars 120 may have a y-directional width that is less than an x-directional length so as to provide sufficient x-y surface area of the pillars for support and/or bonding without unduly increasing the y-directional width and blocking fluid flow in the x-direction.

In some embodiments, one or more additional and/or alternative support mechanisms may be used, such as a pole or pillar that is formed separately from the substrate and/or an external support mechanism such as one or more backings that may cover a front and/or back side of the chip 100.

The magnified circular view in FIG. 1A shows a magnified view of a subset of the plurality of constrictions 106 of chip 100. As shown, the constrictions 106 may be positioned in parallel with one another such that they collectively form a boundary between first fluid flow region 104 and second fluid flow region 108. In the example of chip 100, constrictions 106 are arranged in a straight line (extending in the y-direction) alongside one another. In some embodiments, a set of constrictions in a parallelized flow arrangement with one another may form a boundary in a curved and/or linear shape. In some embodiments, the shape of the boundary may extend diagonally across chip 100 in an x-y plane, thereby increasing its overall length. In some embodiments, the shape of the boundary may extend in a serpentine or step-wise angular manner across chip 100 in an x-y plane, thereby increasing its overall length.

FIG. 1B shows a magnified partial overhead view of chip 100, showing four constrictions 106 of chip 100. As in the circular magnified view in FIG. 1A, the constrictions 106 in FIG. 1B are arranged in a straight line (extending in the y-direction) alongside one another, providing respective flow paths from first fluid flow region 104 on the left to second fluid flow region 108 on the right. In the illustration of FIG. 1B, the uppermost (in the y-direction) of the four constrictions and the surrounding regions are annotated to show the shape and extent of various regions of chip 100. The annotated regions include constriction 106, upstream approach region 112a, downstream approach region 112b, upstream guide channel 114a, and downstream guide channel 114b.

FIG. 1C shows a magnified partial cross-sectional view of chip 100 (showing a cross-sectional z-y plane), showing three constrictions 106 of chip 100. As in FIG. 1A and FIG. 1B, are arranged in a straight line (extending in the y-direction) alongside one another, providing respective flow paths from first fluid flow region 104 to second fluid flow region 108. As shown in FIG. 1C, constrictions 106 may have a height (e.g., an etch depth) that extends in the z-direction, for example extending from the top side of a substrate down into the substrate in the z-direction. In some embodiments, a height of a constriction 106 may be the same as a height of one or more of a corresponding upstream approach region 112a, corresponding downstream approach region 112b, corresponding upstream guide channel 114a, and/or corresponding downstream guide channel 114b.

In some embodiments, dimensions of any one or more of the components shown in FIGS. 1B and/or 1C may be selected in order to increase throughput, decrease clogging, and maintain payload delivery effectiveness and cell viability after delivery.

In some embodiments, a constriction 106 may have a cross-sectional constriction width (in the y-direction as illustrated in FIG. 1B) of greater than or equal to 1.4 µm, 1.6 µm, 1.8 µm, 2.0 µm, 3 µm, 4 µm, 5 µm, 6 µm, or 10 µm. In some, embodiments, the cross-sectional constriction width (in the y-direction as illustrated in FIG. 1B) may be less than or equal to 1.4 µm, 1.6 µm, 1.8 µm, 2.0 µm, 3 µm, 4 µm, 5 µm, 6 µm, or 10 µm. In some embodiments, the cross-sectional constriction width may have a tolerance of ±0.3 µm, ±0.2 µm, ±0.1 µm, or ±0.05 µm. In some embodiments, cross-sectional constriction width may be set and/or selected in accordance with a diameter (e.g., a diameter in suspension) of a cell to be perturbed by passage through the constriction. For example, the ranges recited herein may be configured for processing cells that are between about 1.4 µm and about 10 µm in diameter while in suspension. In light of the disclosure herein, a person of ordinary skill in the art would appreciate that different cross-sectional constriction widths (and other dimensions for a chip corresponding thereto) may be used in use cases where cells of other diameters are to be processed. For example, processing of monocytes may be accomplished with cross-sectional constriction widths that are more than 10 µm; processing of even larger cells may be accomplished with cross-sectional constriction widths of up to about 0.1 mm.

In some embodiments, a constriction 106 may have a constriction length (in the x-direction as illustrated in FIG. 1B) of greater than or equal to 2.5 µm, 5 µm, 7.5 µm, 10 µm, 12.5 µm, 15 µm, 20 µm, 30 µm, 40 µm, 50 µm, 75 µm, 100 µm, 500 µm, 1 mm, 5 mm, 1 cm, or 2 cm. In some, embodiments, the constriction length (in the x-direction as illustrated in FIG. 1B) may be less than or equal to 2.5 µm, 5 µm, 7.5 µm, 10 µm, 12.5 µm, 15 µm, 20 µm, 30 µm, 40 µm, 50 µm, 75 µm, 100 µm, 500 µm, 1 mm, 5 mm, 1 cm, or 2 cm. In some embodiments, the constriction length may have a tolerance of ±2 µm, ±1.5 µm, ±1 µm, or ±0.5 µm.

In some embodiments, a constriction 106 may have a constriction height (in the z-direction as illustrated in FIG. 1C) of greater than or equal to 5 µm, 10 µm, 20 µm, 30 µm, 40 µm, 50 µm, 60 µm, 70 µm, 80 µm, 90 µm, 100 µm, 110 µm, or 120 µm. In some embodiments, constriction height may be less than or equal to 5 µm, 10 µm, 20 µm, 30 µm, 40 µm, 50 µm, 60 µm, 70 µm, 80 µm, 90 µm, 100 µm, 110 µm, or 120 µm. In some embodiments, the constriction height may have a tolerance of ±3 µm, ±2 µm, ±1.5 µm, ±1 µm, or ±0.5 µm.

In some embodiments, a constriction 106 may have a sidewall draft, wherein the sidewall refers to one of the walls that extend vertically in the z-direction as shown in FIG. 1C and define the constriction width. In some embodiments, the sidewall draft may be greater than or equal to 0.01°, 0.02°, 0.03°, 0.04°, 0.05°, or 0.06°. In some embodiments, the sidewall draft may be less than or equal to 0.01°, 0.02°, 0.03°, 0.04°, 0.05°, or 0.06°. In some embodiments, the sidewall draft may have a tolerance of ±0.02°, ±0.01°, or ±0.005°. In some embodiments, a sidewall draft may be greater than or equal to 1°, 2°, 5°, or 10°; in some embodiments, a sidewall draft may be less than or equal to 1°, 2°, 5°, or 10°. Permissible ranges for sidewall draft may depend on z-dimensional constriction heights, because, for a given draft angle, a taller (deeper) constriction may vary in cross-sectional constriction width to a greater extent than a shorter (shallower) constriction would vary. (If variance in constriction width is too significant, then flow of fluid will flow through the wider portions of the constriction instead of through the narrower portions of the constriction, obviating the narrower portions of the channel and possibly allowing fluid to flow through the constriction without perturbing the cell membranes.) Thus, a chip having shorter (shallower) z-dimensional constriction height may be able to have a higher sidewall draft angle than a chip having a taller (deeper) z-dimensional constriction height.

In some embodiments, a constriction 106 may have a sidewall roughness. In some embodiments, the sidewall roughness may be greater than or equal to 0.3 µm, 0.2 µm, 0.15 µm, 0.10 µm, 0.05 µm, 0.01 µm, or 0.001 µm. In some embodiments, the sidewall roughness may be less than or equal to 0.3 µm, 0.2 µm, 0.15 µm, 0.10 µm, or 0.05 µm, 0.01 µm, or 0.001 µm.

In some embodiments, an approach region 112a or 112b may comprise a narrow end and a broad end, wherein the narrow end is proximal to the corresponding constriction 106 and the broad end is proximate to the corresponding guide channel 114a or 114b. An approach region may have side walls that comprise linear walls that angle between the opening at the narrow end and the opening at the broad end, defining an angle of greater than 0° and less than 90° from a straight line in the x-direction. An angle that the approach region side walls make to one another may be greater than 0° and less than 180°. In some embodiments, the side walls of an approach region may comprise one or more curved portions (e.g., defining a serpentine shape when viewed from overhead in the z-direction) and/or corners (e.g., defining a step-like shape when viewed from overhead in the z-direction) between the narrow end and the broad end.

In some embodiments, a cross-sectional approach region width (in the y-direction as illustrated in FIG. 1B) at the narrow end may be greater than or equal to 1.4 µm, 1.6 µm, 1.8 µm, 2.0 µm, 3 µm, 4 µm, 5 µm, 6 µm, or 10 µm. In some embodiments, the cross-sectional approach region width (in the y-direction as illustrated in FIG. 1B) at the narrow end may be less than or equal to 1.4 µm, 1.6 µm, 1.8 µm, 2.0 µm, 3 µm, 4 µm, 5 µm, 6 µm, or 10 µm. In some embodiments, the cross-sectional approach region width at the narrow end may have a tolerance of ±0.3 µm, ±0.2 µm, ±0.1 µm, or ±0.05 µm.

In some embodiments, a cross-sectional approach region width (in the y-direction as illustrated in FIG. 1B) at the broad end may be greater than or equal to 5 µm, 10 µm, 20 µm, 50 µm, 100 µm, 250 µm, or 500 µm. In some embodiments, the cross-sectional approach region width (in the y-direction as illustrated in FIG. 1B) at the broad end may be less than or equal to 5 µm, 10 µm, 20 µm, 50 µm, 100 µm, 250 µm, or 500 µm. In some embodiments, the cross-sectional approach region width at the broad end may have a tolerance of ±0.3 µm, ±0.2 µm, ±0.1 µm, or ±0.05 µm.

In some embodiments, an approach region length (in the x-direction as illustrated in FIG. 1B) may be greater than or equal to 5 µm, 10 µm, 20 µm, 50 µm, 100 µm, 250 µm, or 500 µm. In some, embodiments, an approach region length (in the x-direction as illustrated in FIG. 1B) may be greater than or equal to 5 µm, 10 µm, 20 µm, 50 µm, 100 µm, 250 µm, or 500 µm. In some embodiments, the constriction length may have a tolerance of ±2 µm, ±1.5±µm, or ±0.5 µm.

In some embodiments, an approach region height (in the z-direction as illustrated in FIG. 1C) may be greater than or equal to 5 µm, 10 µm, 20 µm, 30 µm, 40 µm, 50 µm, 60 µm, 70 µm, 80 µm, 90 µm, 100 µm, 110 µm, or 120 µm. In some embodiments, an approach region height (in the z-direction as illustrated in FIG. 1C) may be less than or equal to 5 µm, 10 µm, 20 µm, 30 µm, 40 µm, 50 µm, 60 µm, 70 µm, 80 µm, 90 µm, 100 µm, 110 µm, or 120 µm. In some embodiments, the approach region height may have a tolerance of ±3 µm, ±2 µm, ±1.5 µm, ±1 µm, or ±0.5 µm. In some embodiments, an approach region height may be any suitable height that is less than the height of the substrate in the z-direction.

In some embodiments, an approach region 112a or 112b may have a sidewall draft, wherein the sidewall refers to one of the walls that extend vertically in the z-direction and define the approach region width. In some embodiments, the sidewall draft of the approach region may be greater than or equal to 0.01°, 0.02°, 0.03°, 0.04°, 0.05°, or 0.06°. In some embodiments, the sidewall draft of the approach region may be less than or equal to 0.01°, 0.02°, 0.03°, 0.04°, 0.05°, or 0.06°. In some embodiments, the sidewall draft of the approach region may have a tolerance of ±0.02°, ±0.01°, or ±0.005°. In some embodiments, a sidewall draft may be greater than or equal to 1°, 2°, 5°, or 10°; in some embodiments, a sidewall draft may be less than or equal to 1°, 2°, 5°, or 10°. Permissible ranges for sidewall draft may depend on z-dimensional approach region heights, in a similar manner as discussed above with respect to constriction sidewall draft and constriction heights.

In some embodiments, an approach region 112a or 112b may have a sidewall roughness. In some embodiments, the sidewall roughness of the approach region may be greater than or equal to 0.3 µm, 0.2 µm, 0.15 µm, 0.10 µm, or 0.05 µm. In some embodiments, the sidewall roughness of the approach region may be less than or equal to 0.3 µm, 0.2 µm, 0.15 µm, 0.10 µm, or 0.05 µm.

In some embodiments, an approach region may have side walls that extend from the broad end of the approach region to the narrow end of the approach region. In some embodiments, opposing side walls of an approach region may form an angle with one another that is greater than or equal to 160°, 140°, 120°, 100°, 80°, 60°, 40°, or 20°. In some embodiments, opposing side walls of an approach region may form an angle with one another that is less than or equal to 160°, 140°, 120°, 100°, 80°, 60°, 40°, or 20°. In some embodiments, a side wall of an approach region may form an angle with a side wall of an adjacent constriction that is less than or equal to 80°, 70°, 60°, 50°, 40°, 30°, 20°, or 10°. In some embodiments, a side wall of an approach region may form an angle with a side wall of an adjacent constriction that is greater than or equal to 80°, 70°, 60°, 50°, 40°, 30°, 20°, or 10°.

In some embodiments, a guide channel 114a or 114b may extend between an end proximate a corresponding approach region (112a or 112b) and an opposite end distal from the corresponding approach region.

In some embodiments, a cross-sectional guide channel width (in the y-direction as illustrated in FIG. 1B) may be greater than or equal to 5 µm, 10 µm, 20 µm, 50 µm, 100 µm, 250 µm, or 500 pin. In some embodiments, the cross-sectional guide channel width (in the y-direction as illustrated in FIG. 1B) may be less than or equal to 5 µm, 10 µm, 20 µm, 50 µm, 100 µm, 250 µm, or 500 pin. In some embodiments, the cross-sectional guide channel width may have a tolerance of ±0.3 µm, ±0.2 µm, ±0.1 µm, or ±0.05 µm.

In some embodiments, a guide channel length (in the x-direction as illustrated in FIG. 1B) may be greater than or equal to 5 µm, 10 µm, 20 µm, 50 µm, 100 µm, 250 µm, or 500 µm. In some, embodiments, a guide channel length (in the x-direction as illustrated in FIG. 1B) may be greater than or equal to 5 µm, 10 µm, 20 µm, 50 µm, 100 µm, 250 µm, or 500 µm. In some embodiments, the guide channel length may have a tolerance of ±2 µm, ±1.5 µm, ±1 µm, or ±0.5 µm.

In some embodiments, a guide channel height (in the z-direction as illustrated in FIG. 1C) may be greater than or equal to 5 µm, 10 µm, 20 µm, 30 µm, 40 µm, 50 µm, 60 µm, 70 µm, 80 µm, 90 µm, 100 µm, 110 µm, or 120 µm. In some embodiments, a guide channel height (in the z-direction as illustrated in FIG. 1C) may be less than or equal to 5 µm, 10 µm, 20 µm, 30 µm, 40 µm, 50 µm, 60 µm, 70 µm, 80 µm, 90 µm, 100 µm, 110 µm, or 120 µm. In some embodiments, the guide channel height may have a tolerance of ±3 µm, ±2 µm, ±1.5 µm, ±1 µm, or ±0.5 µm. In some embodiments, a guide channel height may be any suitable height that is less than the height of the substrate in the z-direction.

In some embodiments, a guide channel 114a or 114b may have a sidewall draft, wherein the sidewall refers to one of the walls that extend vertically in the z-direction and define the guide channel width. In some embodiments, the sidewall draft of the guide channel may be greater than or equal to 0.01°, 0.02°, 0.03°, 0.04°, 0.05°, or 0.06°. In some embodiments, the sidewall draft of the approach region may be less than or equal to 0.01°, 0.02°, 0.03°, 0.04°, 0.05°, or 0.06°. In some embodiments, the sidewall draft of the guide channel may have a tolerance of ±0.02°, ±0.01°, or ±0.005°.

In some embodiments, a guide channel 114a or 114b may have a sidewall roughness. In some embodiments, the sidewall roughness of the guide channel may be greater than or equal to 0.3 µm, 0.2 µm, 0.15 µm, 0.10 µm, or 0.05 µm. In some embodiments, the sidewall roughness of the guide channel may be less than or equal to 0.3 µm, 0.2 µm, 0.15 µm, 0.10 µm, or 0.05 µm.

In some embodiments, adjacent parallelized constrictions (and/or corresponding approach regions or guide channels) may be offset from one another in the y-direction by a pitch 116 of less than or equal to 5 µm, 10 µm, 20 µm, 50 µm, 100 µm, 250 µm, or 500 µm. In some embodiments, adjacent parallelized constrictions (and/or corresponding approach regions or guide channels) may be offset from one another in the y-direction by a pitch 116 of greater than or equal to 5 µm, 10 µm, 20 µm, 50 µm, 100 µm, 250 µm, or 500 µm.

In some embodiments, adjacent parallelized constrictions may be separated from one another in the y-direction by a constriction sidewall thickness 118 of less than or equal to 5 µm, 10 µm, 20 µm, 50 µm, 100 µm, 250 µm, or 500 µm. In some embodiments, adjacent parallelized constrictions may be separated from one another in the y-direction by a constriction sidewall thickness 118 of greater than or equal to 5 µm, 10 µm, 20 µm, 50 µm, 100 µm, 250 µm, or 500 µm.

In some embodiments, adjacent parallelized guide channels may be separated from one another in the y-direction by a guide channel sidewall thickness 122 of less than or equal to 5 µm, 10 µm, 20 µm, 50 µm, 100 µm, 200 µm, or 250 µm. In some embodiments, adjacent parallelized guide channels may be separated from one another in the y-direction by a guide channel sidewall thickness 122 of greater than or equal to 5 µm, 10 µm, 20 µm, 50 µm, 100 µm, 200 µm, or 250 µm.

In some embodiments, the substrate in which first flow region 104, constrictions 106, and/or second flow region 108 are formed may have a thickness (in the z-direction) of less than or equal to 300 µm, 400 µm, 600 µm, 800 µm, 1 mm, 2 mm, or 5 mm. In some embodiments, the substrate in which first flow region 104, constrictions 106, and/or second flow region 108 are formed may have a thickness (in the z-direction) of greater than or equal to 300 µm, 400 µm, 600 µm, 800 µm, 1 mm, 2 mm, or 5 mm. A substrate thickness of greater than or equal to about 400 µm may help reduce the risk of the substrate breaking.

In some embodiments, a top layer of chip 100 (e.g., a layer that is placed on top of a substrate layer after the substrate layer is etched) may have a thickness (in the z-direction) of less than or equal to 300 µm, 400 µm, 600 µm, 800 µm, 1 mm, 2 mm, or 5 mm. In some embodiments, a top layer of chip 100 (e.g., a layer that is placed on top of a substrate layer after the substrate layer is etched) may have a thickness (in the z-direction) of greater than or equal to 300 µm, 400 µm, 600 µm, 800 µm, 1 mm, 2 mm, or 5 mm.

In some embodiments, inlet port 102 and/or outlet port 110 may be formed as an opening having a diameter of less than or equal to 200 µm, 400 µm, 500 µm, 1 mm, or 5 mm. In some embodiments, inlet port 102 and or outlet port 11 may be formed as an opening having a diameter of greater than or equal to 200 µm, 400 µm, 500 µm, 1 mm, or 5 mm. In some embodiment the opening may be circular. In some embodiments, the opening may have any shape having a dimension in the y-direction, x-direction, or another direction in the x-y plane that is less than or equal to any of the diameters recited above; in some embodiments, the opening may have any shape having a dimension in the y-direction, x-direction, or another direction in the x-y plane that is greater than or equal to any of the diameters recited above.

In some embodiments, all or part of first fluid region 104 and/or all or part of second fluid region 108 may have a height in the z-direction (e.g., an etch depth into the substrate of chip 100 that is greater than or equal to 5 µm, 10 µm, 20 µm, 30 µm, 40 µm, 50 µm, 60 µm, 70 µm, 80 µm, 90 µm, 100 µm, 110 µm, or 120 µm. In some embodiments, a height (in the z-direction) of all or part of first fluid region 104 and/or all or part of second fluid region 108 may be less than or equal to 5 µm, 10 µm, 20 µm, 30 µm, 40 µm, 50 µm, 60 µm, 70 µm, 80 µm, 90 µm, 100 µm, 110 µm, or 120 µm. In some embodiments, the height of first fluid region 104 and/or the height of second fluid region 108 may have a tolerance of ±3 µm, ±2 µm, ±1.5 µm, ±1 µm, or ±0.5 µm In some embodiments, any one or more of constrictions 106 may be characterized by a quotient of a cross-sectional constriction area over a cross-sectional constriction perimeter. In some embodiments, the quotient of the cross-sectional constriction area over the cross-sectional constriction perimeter may be greater than or equal to 0.5 µm, 0.75 µm, 0.9 µm, 1.0 µm, 1.1 µm, 1.25 µm, 1.5 µm, 2 µm, 3 µm, or 5 µm. In some embodiments, the quotient of the cross-sectional constriction area over the cross-sectional constriction perimeter may be less than or equal to 0.5 µm, 0.75 µm, 0.9 µm, 1.0 µm, 1.1 µm, 1.25 µm, 1.5 µm, 2 µm, 3 µm, or 5 µm. In some embodiments, constrictions in which this quotient is higher may be less prone to clogging than constrictions in which the quotient is lower. In some embodiments, for a given constriction width (which may be dictated by cell diameters (e.g., a diameter of the cell in suspension) of the cell(s) to be perturbed by passage through the constriction), constrictions in which this quotient is higher may be less prone to clogging than constrictions in which the quotient is lower. In some embodiments, increasing this quotient may be achieved by etching deep, narrow, rectangular constrictions (e.g., slit-shaped constrictions) into a substrate (e.g., a silicon substrate) as described herein. The constrictions may be formed by etching sufficiently deeply and/or depositing constriction sidewall material while maintaining constriction sidewalls within a sufficient angular threshold of parallel to one another as described herein. Furthermore, the constrictions may be formed by etching sufficiently deeply and/or depositing constriction sidewall material while maintaining the sidewalls within a predefined envelope (e.g., tolerance) of distance from one another, such that a cell forced through the constriction may be deformed by the side walls regardless of the location (e.g., the etch depth) at which the cell passes through the constriction. In this way, each deep, narrow, rectangular constriction may have an increased individual throughput, due to a larger cross-sectional constriction area, as compared to constrictions that have widths configured to perturb cells of the same diameter but that are not etched as deeply into a substrate. Furthermore, because clogging of constrictions may be caused by the edges and corners of the constrictions, deep, narrow, rectangular constrictions may clog at a decreased rate as compared to constrictions that have widths configured to perturb cells of the same diameter but that are not etched as deeply into a substrate. In some embodiments, thus, increasing cross-sectional constriction area while minimizing cross-sectional constriction perimeter may increase per-constriction throughput while minimizing likelihood and/or extent of constriction clogging.

In some embodiments, pillars 120 that are surrounded by first fluid flow region 104 may have a collective total surface area in an x-y plane that is 5-10% of an area in the x-y plane of first fluid flow region 104 itself. In some embodiments, pillars 120 that are surrounded by first fluid flow region 104 may have a collective total surface area in an x-y plane that is less than or equal to 1%, 5%, 10%, 15%, 20%, 25%, or 50% of the area in the x-y plane of first fluid flow region 104 itself. In some embodiments, pillars 120 that are surrounded by first fluid flow region 104 may have a collective total surface area in an x-y plane that is greater than or equal to 1%, 5%, 10%, 15%, 20%, 25%, or 50% of the area in the x-y plane of first fluid flow region 104 itself.

In some embodiments, pillars 120 that are surrounded by second fluid flow region 108 may have a collective total surface area in an x-y plane that is 5-10% of an area in the x-y plane of second fluid flow region 108 itself. In some embodiments, pillars 120 that are surrounded by second fluid flow region 108 may have a collective total surface area in an x-y plane that is less than or equal to 1%, 5%, 10%, 15%, 20%, 25%, or 50% of the area in the x-y plane of second fluid flow region 108 itself. In some embodiments, pillars 120 that are surrounded by first fluid flow region 108 may have a collective total surface area in an x-y plane that is greater than or equal to 1%, 5%, 10%, 15%, 20%, 25%, or 50% of the area in the x-y plane of first fluid flow region 108 itself.

In some embodiments, chip 100 may have an overall chip length in the x-direction of greater than or equal to 2 mm, 4 mm, 10 mm, 20 mm, 30 mm, 40 mm, 50 mm, 100 mm, 250 mm, 450 mm, or 500 mm. In some embodiments, chip 100 may have an overall chip length in the x-direction of less than or equal to 2 mm, 4 mm, 10 mm, 20 mm, 30 mm, 40 mm, 50 mm, 100 mm, 250 mm, 450 mm, or 500 mm.

In some embodiments, chip 100 may have an overall chip width in the y-direction of greater than or equal to 2 mm, 4 mm, 10 mm, 20 mm, 30 mm, 40 mm, 50 mm, 100 mm, 250 mm, 450 mm, or 500 mm. In some embodiments, chip 100 may have an overall chip width in the y-direction of less than or equal to 2 mm, 4 mm, 10 mm, 20 mm, 30 mm, 40 mm, 50 mm, 100 mm, 250 mm, 450 mm, or 500 mm.

In some embodiments, chip 100 may have an overall chip height (e.g., thickness) in the z-direction of less than or equal to 300 µm, 400 µm, 600 µm, 800 µm, 1 mm, 2 mm, 3 mm, or 5 mm. In some embodiments, chip 100 may have an overall chip height (e.g., thickness) in the z-direction of greater than or equal to 300 µm, 400 µm, 600 µm, 800 µm, 1 mm, 2 mm, 3 mm, or 5 mm. In some embodiments, the overall chip height may be between 400 µm and 3 mm.

In some embodiments, an etched area forming the first fluid flow region 104 and the second fluid flow region 108 may have a combined surface area (e.g., in an x-y plane) that is less than or equal to 75%, 50%, 40%, 30%, 20%, or 10% of a surface area of the microfluidic chip and/or of the substrate into which the flow regions are etched. In some embodiments, the etched area may have a combined surface area that is greater than or equal to 75%, 50%, 40%, 30%, 20%, or 10% of the surface area of the microfluidic chip and/or of the substrate into which the flow regions are etched.

In some embodiments, chip 100 may have a substrate (e.g., a silicon substrate) into which constrictions are etched having a substrate thickness in the z-direction of less than or equal to 300 µm, 400 µm, 600 µm, 800 µm, 1 mm, 2 mm, or 3 mm. In some embodiments, chip 100 may have a substrate (e.g., a silicon substrate) into which constrictions are etched having a substrate thickness in the z-direction of greater than or equal to 300 µm, 400 µm, 600 µm, 800 µm, 1 mm, 2 mm, or 3 mm.

In some embodiments, the set of parallelized constrictions may include 1001-1500 constrictions, 1501-2000 constrictions, 2001-2500 constrictions, 2501-5000 constrictions, or 5001-10000 constrictions. In some embodiments, the set of parallelized constrictions 106 in chip 100 may include greater than or equal to 1, 5, 10, 25, 50, 100, 250, 500, 1000, 2,500, or 5,000 parallelized constrictions. In some embodiments, the set of parallelized constrictions 106 in chip 100 may include a fewer than or equal to 1, 5, 10, 25, 50, 100, 250, 500, 1000, 2,500, or 5,000 parallelized constrictions. Chips having a relatively large number of parallelized constrictions, as disclosed herein, may enable high volumetric flow rate of a cell suspension, high cell throughput, and decreased clogging.

In some embodiments, chip 100 may comprise one or more components made of metal, plastic, polymers, and/or glass. In some embodiments, a substrate of chip 100 may comprise silicon. In some embodiments, a top layer of chip 100 (e.g., a layer bonded or affixed atop a substrate layer) may comprise glass and/or quartz.

In the example shown in FIG. 1B, constrictions 106 have a rectangular cross-sectional shape, as viewed from the overhead angle depicted in FIG. 1B. Thus, the constrictions 106 shown in FIG. 1B have a uniform cross-sectional constriction width (in the y-direction, as illustrated in FIG. 1B) at all points along the length (in the x-direction). In some additional or alternative embodiments, a constriction (such as constrictions 106) may have a trapezoidal, curved, stepped, or otherwise irregular cross-sectional shape, as viewed from the overhead angle depicted in FIG. 1B.

For example, in some embodiments, rather than having a uniform cross-sectional constriction width (in the y-direction as illustrated in FIG. 1B), a constriction may have a tapered shape such that its cross-sectional width in the y-direction increases or decreases (linearly or otherwise) along the length (in the x-direction) of the constriction. In some embodiments, the cross-sectional width of a tapering constriction may increase or decrease (from any of the cross sectional constriction widths given herein) along the length of the entire constriction by about 1%, 2%, 3%, 5%, 10%, 25%, 50%, 100%, 200%, or 500%.

In some embodiments, rather than having a uniform cross-sectional constriction width (in the y-direction as illustrated in FIG. 1B), a constriction may have a multi-stage constriction width, wherein the constriction has a stepped shape in which a plurality of stages of the constriction (in the x-direction as illustrated in FIG. 1B) have differing cross-sectional widths from one or more of the other stages. For example, in some embodiments, a constriction may have two stages in which a first stage is narrower than a second stage, or in which the second stage is narrower than the first stage. Cross-sectional widths of constriction stages may increase monotonically in the direction of flow in the constriction, may decrease monotonically in the direction of flow of the constriction, or may both increase and decrease in the direction of flow of the constriction (for example, in the case of a constriction having three or more constriction stages). Stages may be differentiated from one another by steps (in the y-direction) formed in one constriction wall or in both constriction walls. Steps between stages in a constriction may be formed as a right-angle step and/or may be formed by a tapered transition region between the steps.

In some embodiments, any one or more constriction stages may have a cross-sectional constriction width equal to any of the cross-sectional constriction widths disclosed herein. In some embodiments, adjacent constriction stages may have cross-sectional constriction widths that vary from one another by about 1%, 2%, 3%, 5%, 10%, 25%, 50%, 100%, 200%, or 500%.

In some embodiments, any one or more constriction stages may have a constriction length equal to any of the constriction lengths disclosed herein. Alternatively, a set of constriction stages forming an entire constriction may have lengths that sum to equal any of the constriction lengths disclosed herein.

In some embodiments in which adjacent constriction stages are separated by a tapering constriction transition region, the length of the tapering constriction transition region may be equal to about 0.1%, 0.5%, 1%, 2%, 3%, 5%, 10%, 25%, 50%, or 100% of any of the constriction lengths disclosed herein.

In some embodiments, constrictions of non-uniform (e.g., tapering) cross-sectional width and/or constrictions having multiple stages of different cross-sectional widths may allow for the chip to extend the amount of time for which a cell passing through the constriction is subject to pressure from the constriction walls, thereby extending the amount of time that pores in the cell wall are open and increasing payload delivery efficiency and effectiveness. In some embodiments, a constriction having an initial narrower portion followed by a subsequent wider portion may allow for pores to be formed quickly and effectively in the initial portion and for the pores to be caused to remain open as the cell passes through the wider portion. Using a wider constriction portion subsequent to a narrower constriction portion may achieve effective payload delivery while increasing cell viability as compared to implementations in which the entire constriction has the narrower constriction width.

FIGS. 2A-2B illustrate steps of fabrication of chip for delivering a payload to a cell, in accordance with some embodiments. Specifically, FIG. 2A illustrates a partial cross-sectional view of a constriction of a chip, e.g., a constriction 106 of chip 100, following an etching step, in accordance with some embodiments; FIG. 2B illustrates a partial cross-sectional view of the constriction of the chip following a deposition step that is performed after the etching step, in accordance with some embodiments.

As shown in FIG. 2A, an etching step for forming a constriction in a chip may include etching down (e.g., down in the z-direction) into a substrate of the chip to remove material from the substrate to form a channel therein. In some embodiments, the etching step may include dry etching and/or wet etching. In some embodiments, the etching step may include deep reactive ion etching.

In some embodiments, the etched channel may have one or more dimensions (e.g., height in the z-direction and/or width in the y-direction) that is larger than a target dimension of the constriction at the end of the fabrication process (e.g., following deposition).

As shown in FIG. 2B, following the etching step, a deposition step may be performed in which a layer of material is deposited onto the etched substrate. In some embodiments, the deposited material may include SiO, plastic, glass, silicon-derived materials, plastic-derived materials, glass-derived materials, metals (e.g., gold, silver, stainless steel, and/or aluminum), and/or metal-derived materials. In some embodiments, deposition of this layer of material may cause the etched channel to be narrowed by material that is deposited on the vertical (z-directional)

side-walls of the channel, and the channel may be narrowed by this deposition process to form the constriction having desired constriction dimensions.

In some embodiments, the deposited layer may have a thickness of greater than or equal to 10 nm, 50 nm, 100 nm, 500 nm, 1 μm, or 2 μm. In some embodiments, the deposited layer may have a thickness of less than or equal to 10 nm, 50 nm, 100 nm, 500 nm, 1 μm, or 2 μm.

In some embodiments, the constriction following the deposition step may have one or more dimensions that are the same as any of the dimensions of constrictions 106 described with reference to FIGS. 1A-1C.

Flow Properties of Microfluidic Chips Disclosed Herein

Described below are various fluid flow characteristics of fluids flowing through a microfluidic chip described herein, along with various chip properties that may affect fluid flow characteristics. Specifically, provided below are pressures, shear stresses, shear rates, cell flow rates, cell volumetric flow rate, cell clogging rates, and cell throughputs.

As explained above, microfluidic chips provided herein are designed to operate under pressure to ensure that the cells of a cell suspension are forced from an upstream fluid flow region through a constriction to a downstream fluid flow region, such that a cell membrane of the cell is perturbed by passage through the constriction. In some embodiments, microfluidic chip 100 may be configured to operate at 1-200 PSI, 10-150 PSI, or 25-100 PSI. In some embodiments, microfluidic chip 100 may be configured to operate at pressures of less than or equal to 1, 5, 10, 25, 50, 75, 100, 125, 150, or 200 PSI. In some embodiments, microfluidic chip 100 may be configured to operate at pressures of greater than or equal to 1, 5, 10, 25, 50, 75, 100, 125, 150, or 200 PSI.

In some embodiments, microfluidic chip 100 may provide a fluid flow velocity through a constriction of the chip of greater than or equal to 0.5 m/s, 1 m/s, 5 m/s, 10 m/s, 15 m/s, 20 m/s, 25 m/s, 30 m/s, 40 m/s or 50 m/s. In some embodiments, microfluidic chip 100 may provide a fluid flow velocity through a constriction of the chip of less than or equal to 0.5 m/s, 1 m/s, 5 m/s, 10 m/s, 15 m/s, 20 m/s, 25 m/s, 30 m/s, 40 m/s or 50 m/s.

As explained above, microfluidic chips provided herein are specifically designed to have a high throughputs. Due to the particular constriction geometry, the number of cells that can pass through the constriction (and become perturbed by the constriction) is greater than known microfluidic chips for a given unit of time.

In some embodiments, microfluidic chip 100 may provide a volumetric flow rate through a single constriction of the chip of greater than or equal to 0.5 μL/min, 1 μL/min, 10 μL/min, 100 μL/min, 500 μL/min, 1 mL/min, or 5 mL/min. In some embodiments, microfluidic chip 100 may provide a volumetric flow rate through a single constriction of the chip of less than or equal to 0.5 μL/min, 1 μL/min, 10 μL/min, 100 μL/min, 500 μL/min, 1 mL/min, or 5 mL/min.

In some embodiments, microfluidic chip 100 may provide an overall volumetric flow rate (combined across all parallelized constrictions 106) of greater than or equal to 0.5 mL/min, 1 mL/min, 10 mL/min, 100 mL/min, 500 mL/min, 1 L/min, or 5 L/min. In some embodiments, microfluidic chip 100 may provide an overall volumetric flow rate (combined across all parallelized constrictions 106) of less than or equal to 0.5 mL/min, 1 mL/min, 10 mL/min, 100 mL/min, 500 mL/min, 1 L/min, or 5 L/min.

In some embodiments, microfluidic chip 100 may provide a cell throughput rate through a constriction of the chip of less than or equal to 5 mL/min, 10 mL/min, 15 mL/min, 20 mL/min, 30 mL/min, or 50 mL/min. In some embodiments, microfluidic chip 100 may provide a cell throughput rate through a constriction of the chip of greater than or equal to 5 mL/min, 10 mL/min, 15 mL/min, 20 mL/min, 30 mL/min, or 50 mL/min.

In some embodiments, microfluidic chip 100 may provide an overall cell throughput rate of less than or equal to 5 mL/min, 10 mL/min, mL/min, 50 mL/min, 100 mL/min, 200 mL/min, or 500 mL/min. In some embodiments, microfluidic chip 100 may provide an overall cell throughput rate of greater than or equal to 5 mL/min, 10 mL/min, mL/min, 50 mL/min, 100 mL/min, 200 mL/min, or 500 mL/min.

Microfluidic chips described herein have been designed to minimize cell clogging in the fluid flow regions and/or constrictions. The number of cells required to clog a microfluidic chip according to embodiments provided herein is dependent upon the cross-sectional area of a constriction, particle/cell diameter, and particle/cell flow rate. This relationship can be defined as:

$$n_{max} \alpha \frac{AD}{2V_P}, A = \text{cross sectional area}, D = \text{particle diameter},$$

$$V = \text{particle flow rate}$$

Below, FIGS. 3A-3C, 4, 5A-5C, and 6A-6C illustrate various embodiments of chips that may have different flow properties, such as embodiments having approach regions with sidewalls at different angles.

Figure 3A:
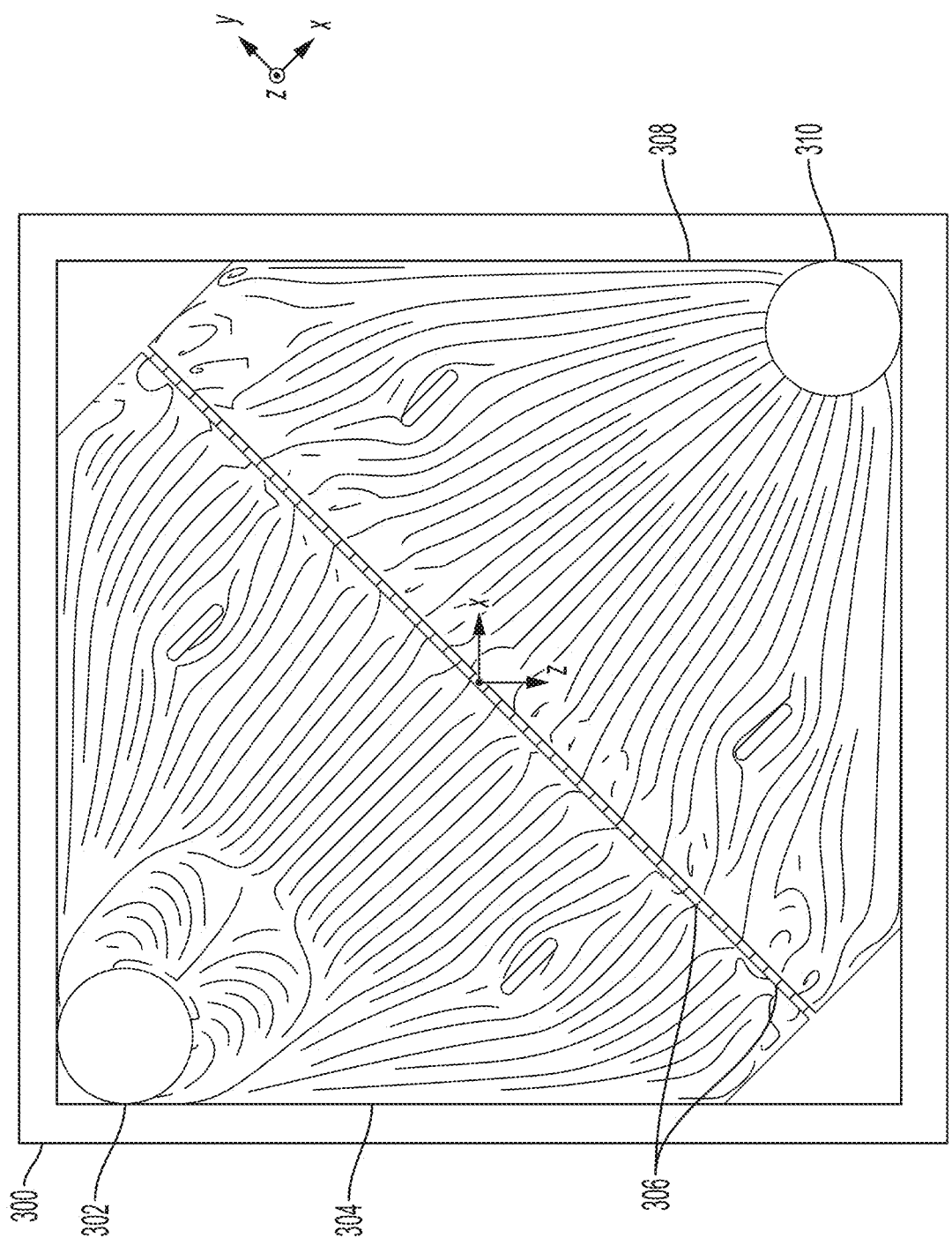
FIGS. 3A-3C illustrate various views at different magnifications of flow lines showing flow patterns of a cell suspension through a chip for delivering a payload to a cell, wherein the chip does not have angled approach regions, in accordance with some embodiments.
Figure 3B:
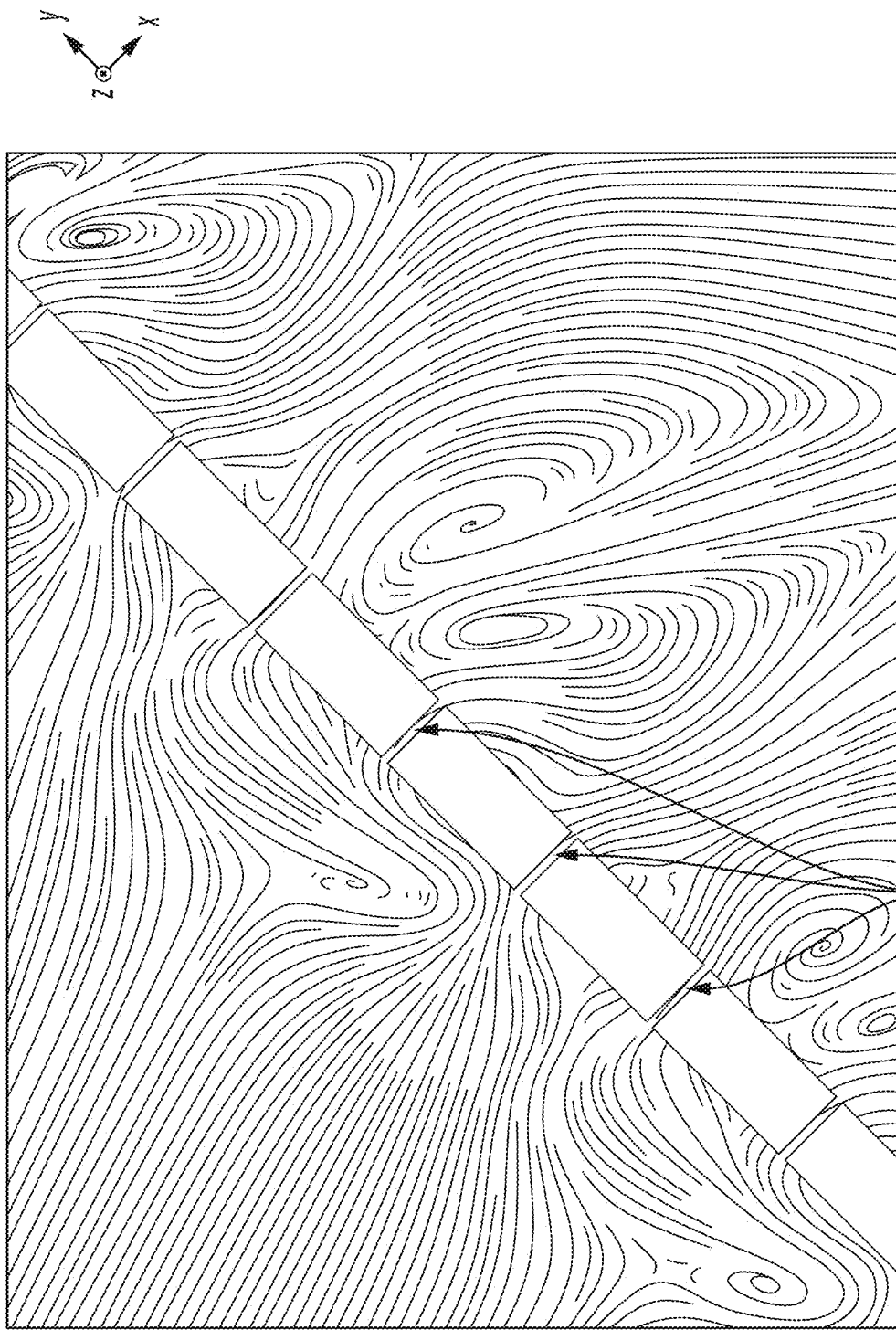
Figure 3C:
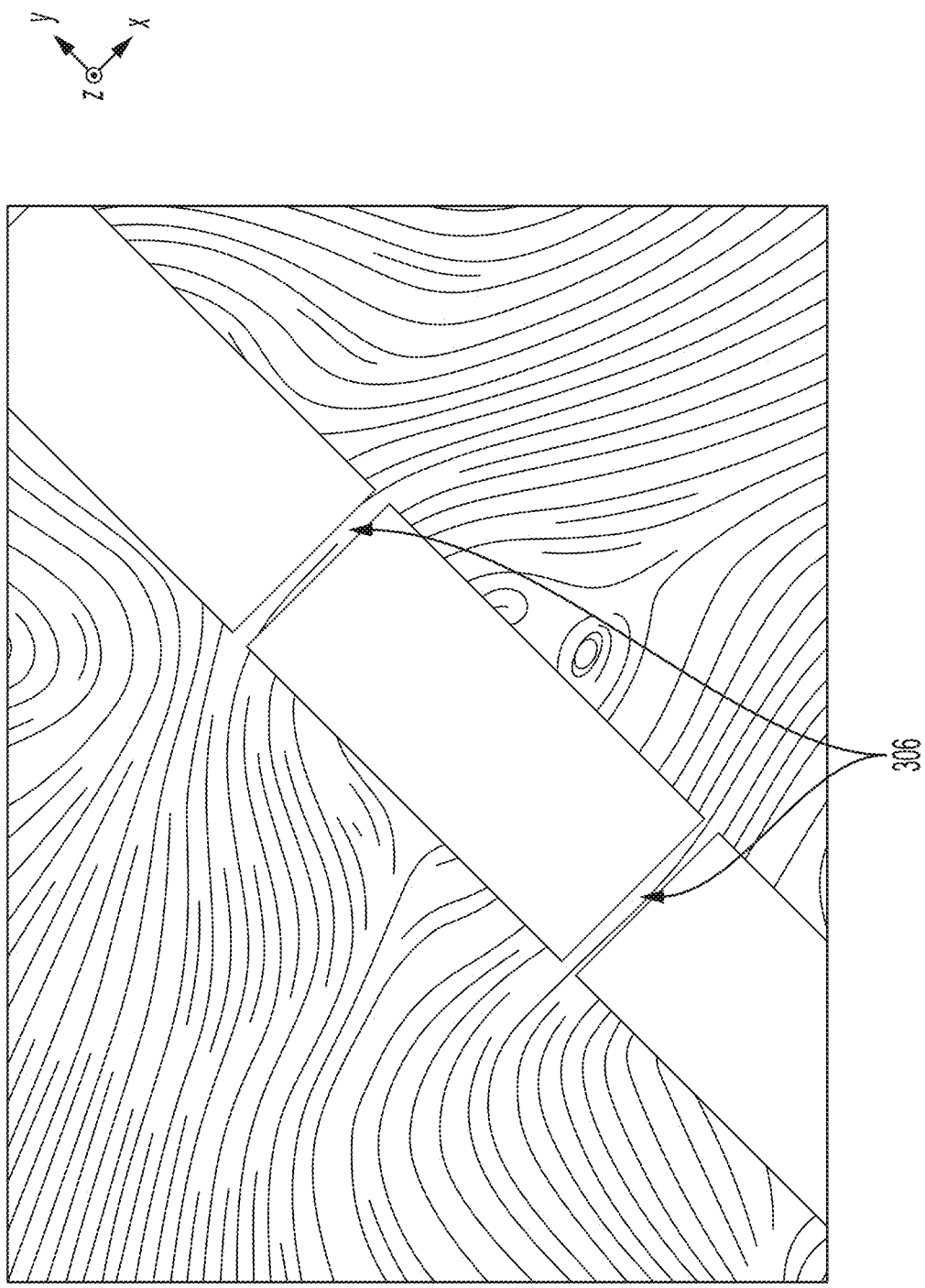

FIGS. 3A-3C illustrate various views at different magnifications of flow lines showing flow patterns of a cell suspension through an exemplary microfluidic chip 300 for delivering a payload to a cell, wherein the chip does not have angled approach regions, in accordance with some embodiments.

FIG. 3A shows chip 300, which includes inlet port 302, first flow region 304, constrictions 306, second flow region 308, and outlet port 310. The components of chip 300 may share any one or more characteristics in common with corresponding (e.g., similarly numbered) components of chip 100 described above with respect to FIGS. 1A-1C. FIG. 3B shows a magnified partial view of chip 300, including several of the constrictions 306. FIG. 3C shows a further magnified partial view of chip 300, including two of the constrictions 306.

As shown in FIGS. 3A-3C, chip 300 does not have tapered or angled approach regions adjacent to constrictions 306. Rather, the side walls of constrictions 306 for right angles with the end walls of first flow region 304 and second flow region 308.

In chip 300, fluid (e.g., cell suspension) may flow in the x-axis dimension (diagonally on the page in FIGS. 3A-3C) from inlet port 302 to outlet port 310. The curved black lines throughout first flow region 304, second flow region 308 and constrictions 306 demonstrate flow patterns of fluid (e.g., a cell suspension) flowing throughout chip 300. Swirls in the patterns indicate interruption in flow, and cells of a cell suspension may aggregate at points where flow is interrupted. Flat points in the flow patterns indicate areas at which cells may aggregate during flow. Points in the flow patterns at which lines diverge indicate areas at which cells may aggregate.

Figure 4:
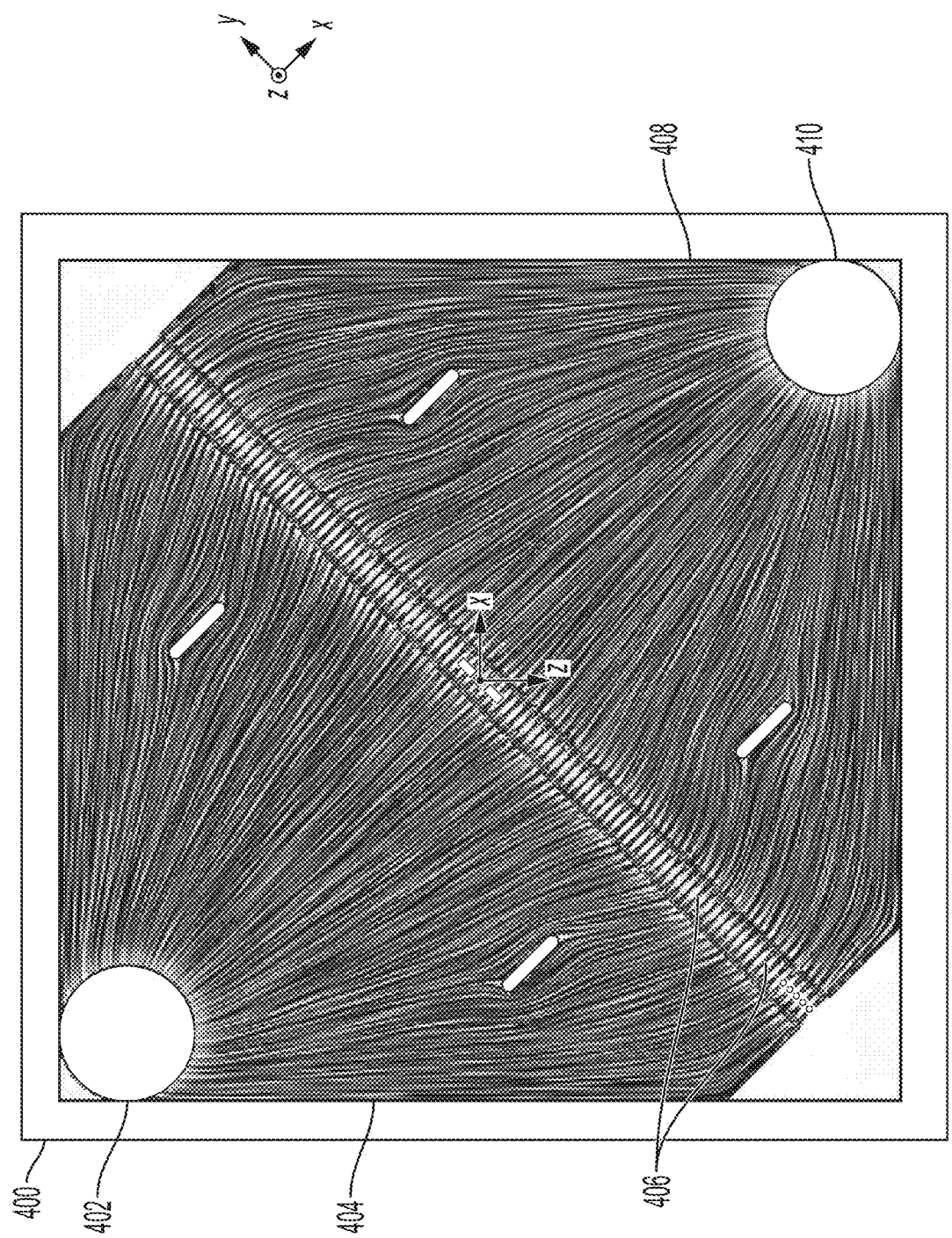
FIG. 4 illustrates flow lines showing flow patterns of a cell suspension through a chip for delivering a payload to a cell, wherein the chip has angled approach regions, in accordance with some embodiments.

FIG. 4 illustrates flow lines showing flow patterns of a cell suspension through an exemplary microfluidic chip 400 for delivering a payload to a cell, wherein the chip has angled approach regions, in accordance with some embodiments.

FIG. 4 shows chip 400, which includes inlet port 402, first flow region 404, constrictions 406, second flow region 408, and outlet port 410. The components of chip 400 may share any one or more characteristics in common with corresponding (e.g., similarly numbered) components of chip 100 described above with respect to FIGS. 1A-1C and/or with chip 300 described above with respect to FIGS. 3A-3C.

Chip 400 may differ from chip 300 in that constrictions 406 may have tapered approach regions adjacent to each respective constriction. In the example shown, chip 400 has approach regions that have side walls converging toward constrictions 406 at a 20° angle and diverging from constrictions 406 at 20° angles (wherein the angles are defined by the angle that opposing approach-region sidewalls make with one another).

In chip 400, fluid (e.g., cell suspension) may flow in the x-axis dimension (diagonally on the page in FIG. 4) from inlet port 402 to outlet port 410. The curved black lines throughout first flow region 404, second flow region 408 and constrictions 406 demonstrate flow patterns of fluid (e.g., a cell suspension) flowing throughout chip 400.

The same convention for representing flow patterns is used with FIG. 4 as was used for FIGS. 3A-3C, such that swirls in the patterns indicate interruption in flow, flat points in the flow patterns indicate areas at which cells may aggregate during flow, and points in the flow patterns at which lines diverge indicate areas at which cells may aggregate. Thus, it should be noted that the flow patterns in FIG. 4 are smoother, more uniform, and less chaotic than the flow patterns in FIGS. 3A-3C, indicating that approach regions having tapered side walls may improve flow in a microfluidic chip, may help avoid aggregation of cells and/or clogging of the chip, and may improve throughput of a chip, and may improve usable lifespan of a chip.

Figure 5A:
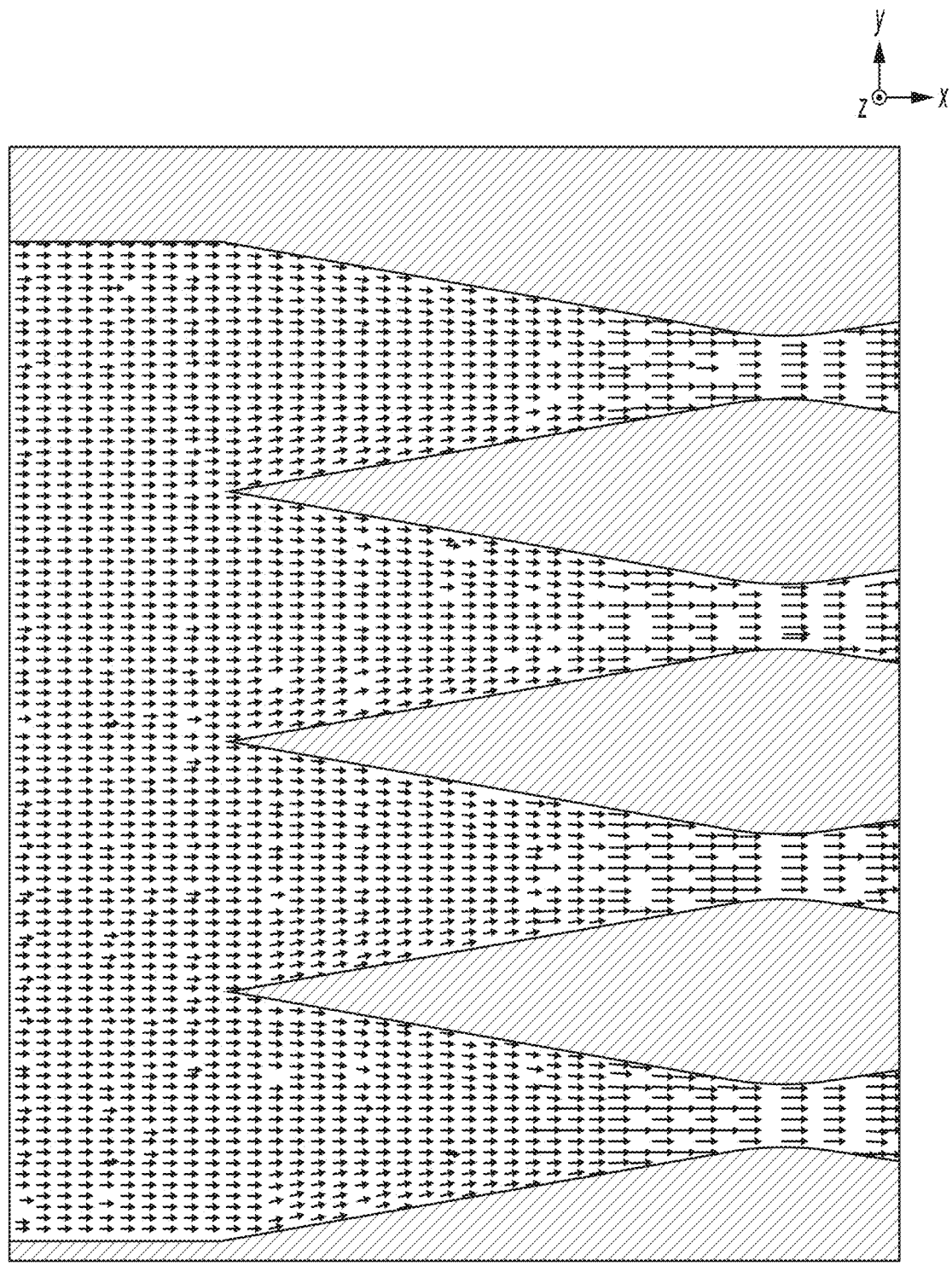
FIGS. 5A-5C illustrate flow lines showing flow patterns of a various cell suspensions through different embodiments of a chip for delivering payloads to cells, wherein the embodiments have approach regions defined by different respective angles (or, in the case of FIG. 5C, the embodiment does not have angled approach regions adjacent the constrictions).
Figure 5B:
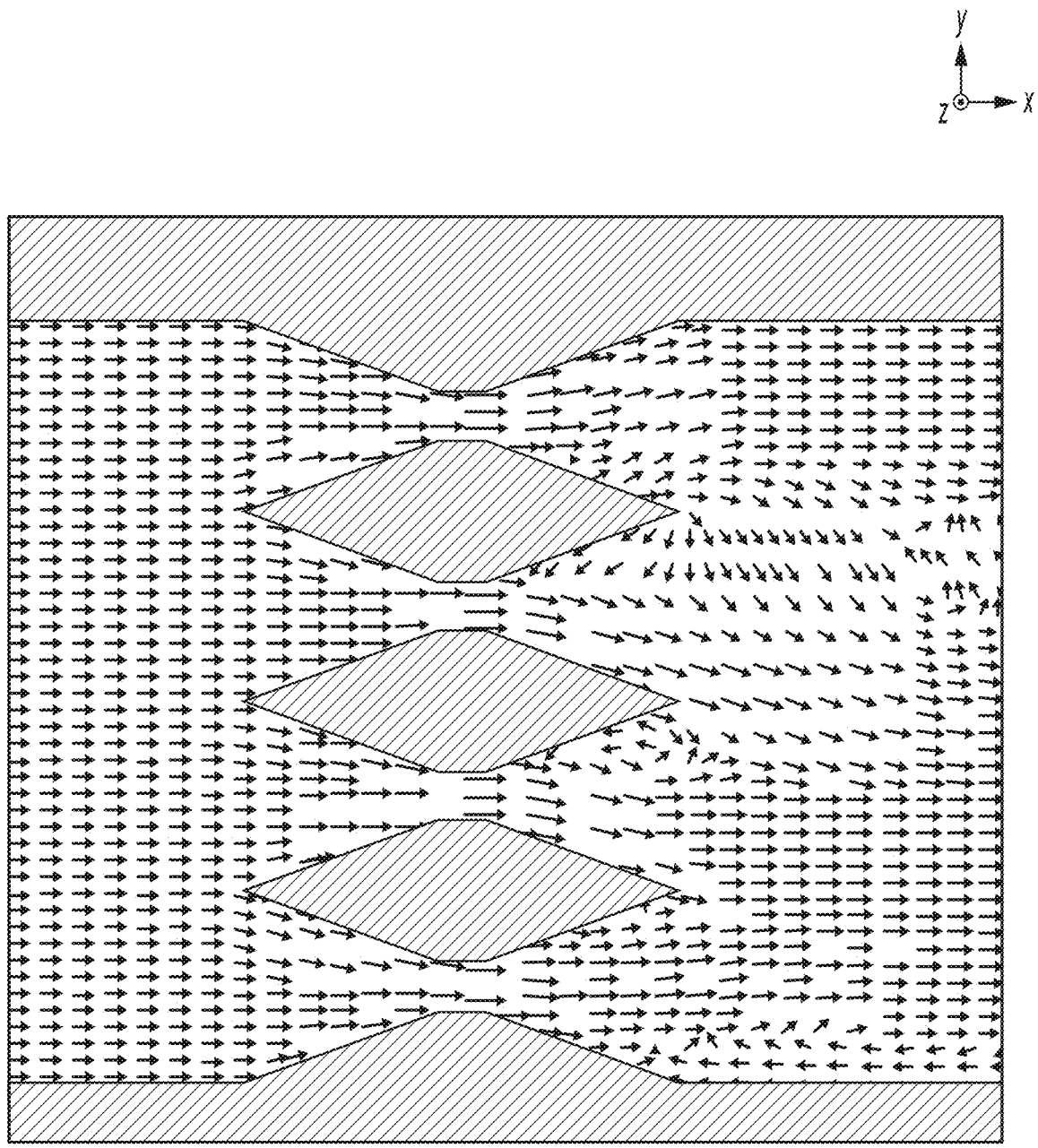
Figure 5C:
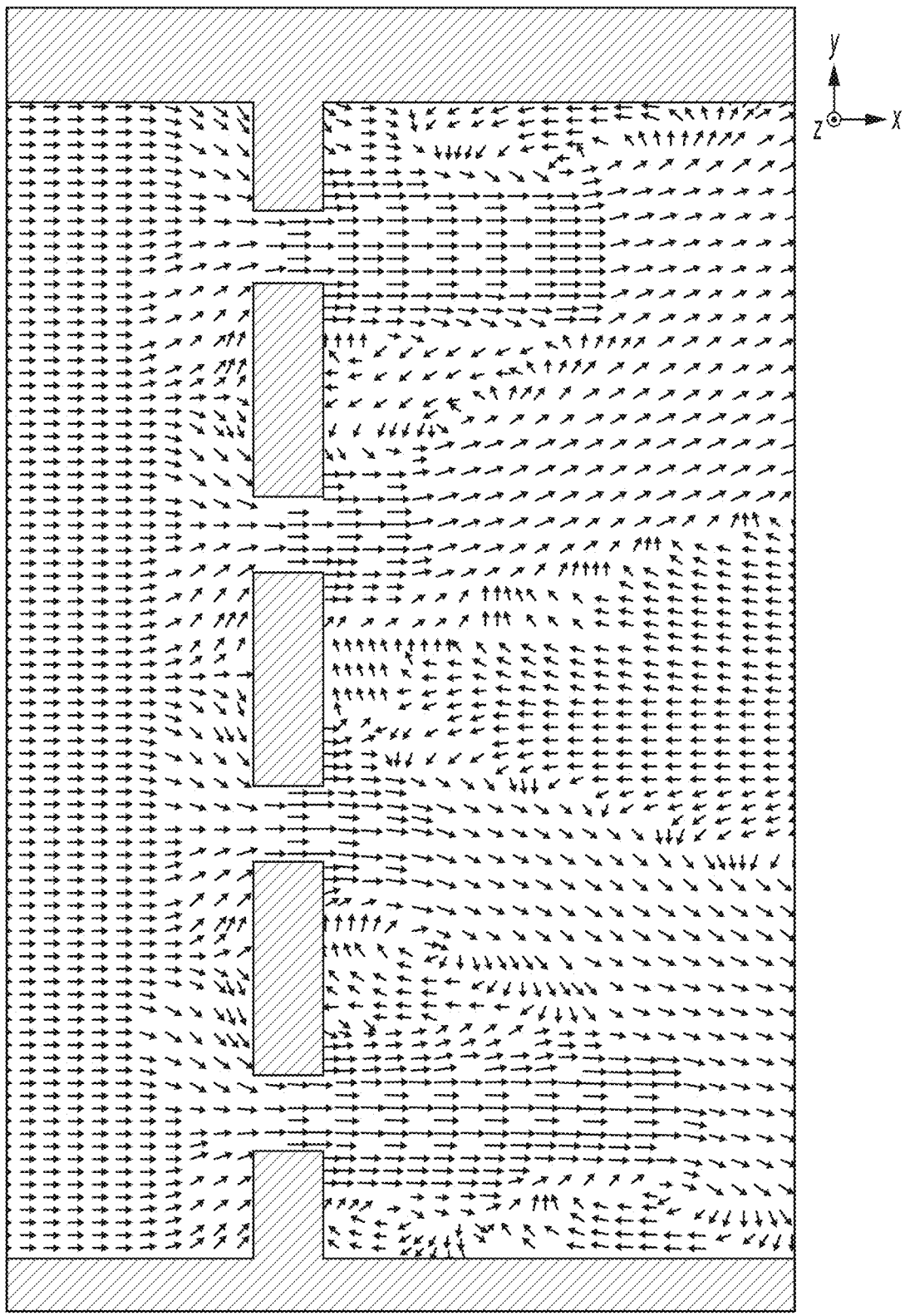

FIGS. 5A-5C illustrate flow lines showing flow patterns of a various cell suspensions through different embodiments of a chip for delivering payloads to cells, wherein the embodiments have approach regions defined by different respective angles (or, in the case of FIG. 5I, the embodiment does not have angled approach regions adjacent the constrictions).

The embodiments shown in FIGS. 5A-5C show partial close-up views of a chip that may share some or all characteristics in common with chips (and components thereof) described above with reference to FIGS. 1A-1C, 3A-3C, and/or 4. In the embodiments shown in FIGS. 5A-5C, fluid (e.g., a cell suspension) may flow in the x-axis direction from left to right on the page through the illustrated constrictions.

The chip embodiments in FIGS. 5A-5B have approach regions defined by different respective angles, and, in the case of FIG. 5C, the embodiment does not have angled approach regions adjacent the constrictions. The embodiment in FIG. 5A has approach regions with sidewalls that form a 20° angle with their respective opposite sidewalls; FIG. 5B shows a 40° angle embodiment; and FIG. 5C does not include any tapered or angled approach regions, similar to as shown in FIGS. 3A-3C (this may be referred to as a "180° angle embodiment").

Fluid flow patterns in the various embodiment of FIGS. 5A-5C are illustrated by the arrows shown in the fluid flow regions, approach regions, and constrictions. As shown, the fluid flow patterns are generally smoother, more uniform, and less chaotic for embodiments having more gradually angled approach regions, indicating that approach regions with more gradually angling sidewalls may improve flow in a microfluidic chip, may help avoid aggregation of cells and/or clogging of the chip, and may improve throughput of a chip, and may improve usable lifespan of a chip.

Figure 6A:
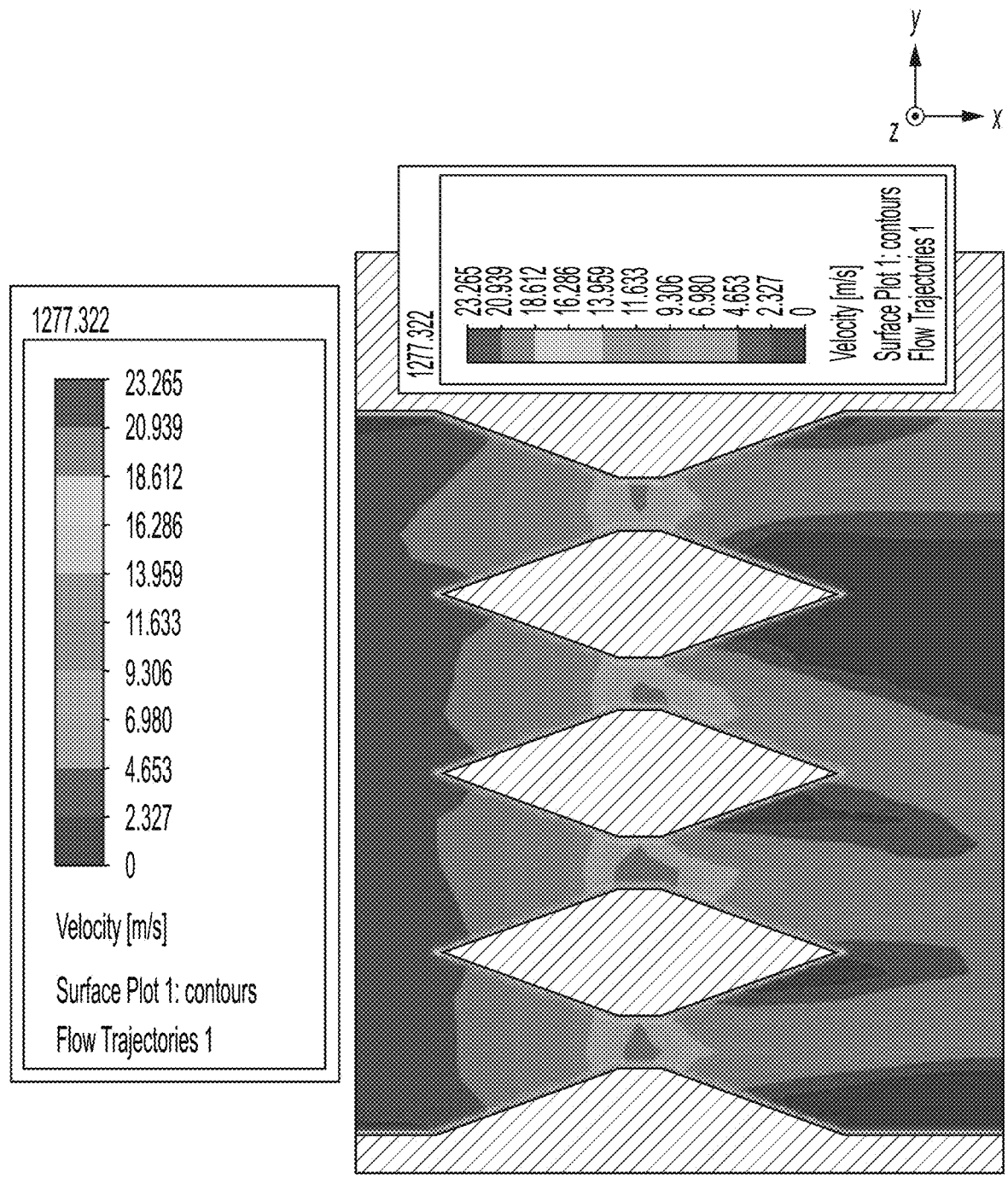
FIGS. 6A-6C illustrate flow velocities of a various cell suspensions through different embodiments of a chip for delivering payloads to cells, wherein the embodiments have approach regions defined by different respective angles (or, in the case of FIG. 5I, the embodiments does not have angled approach regions adjacent the constrictions).
Figure 6B:
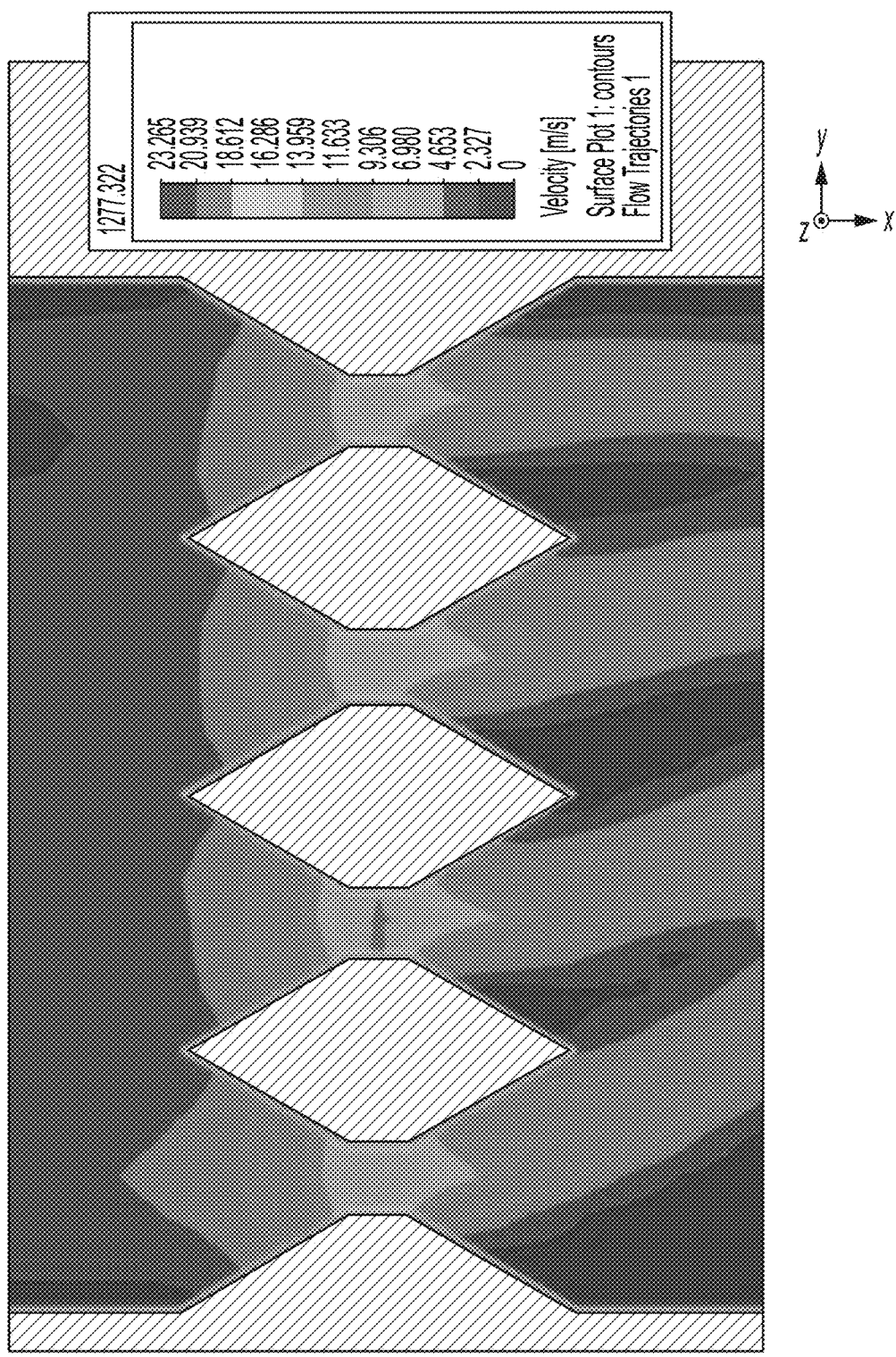
Figure 6C:
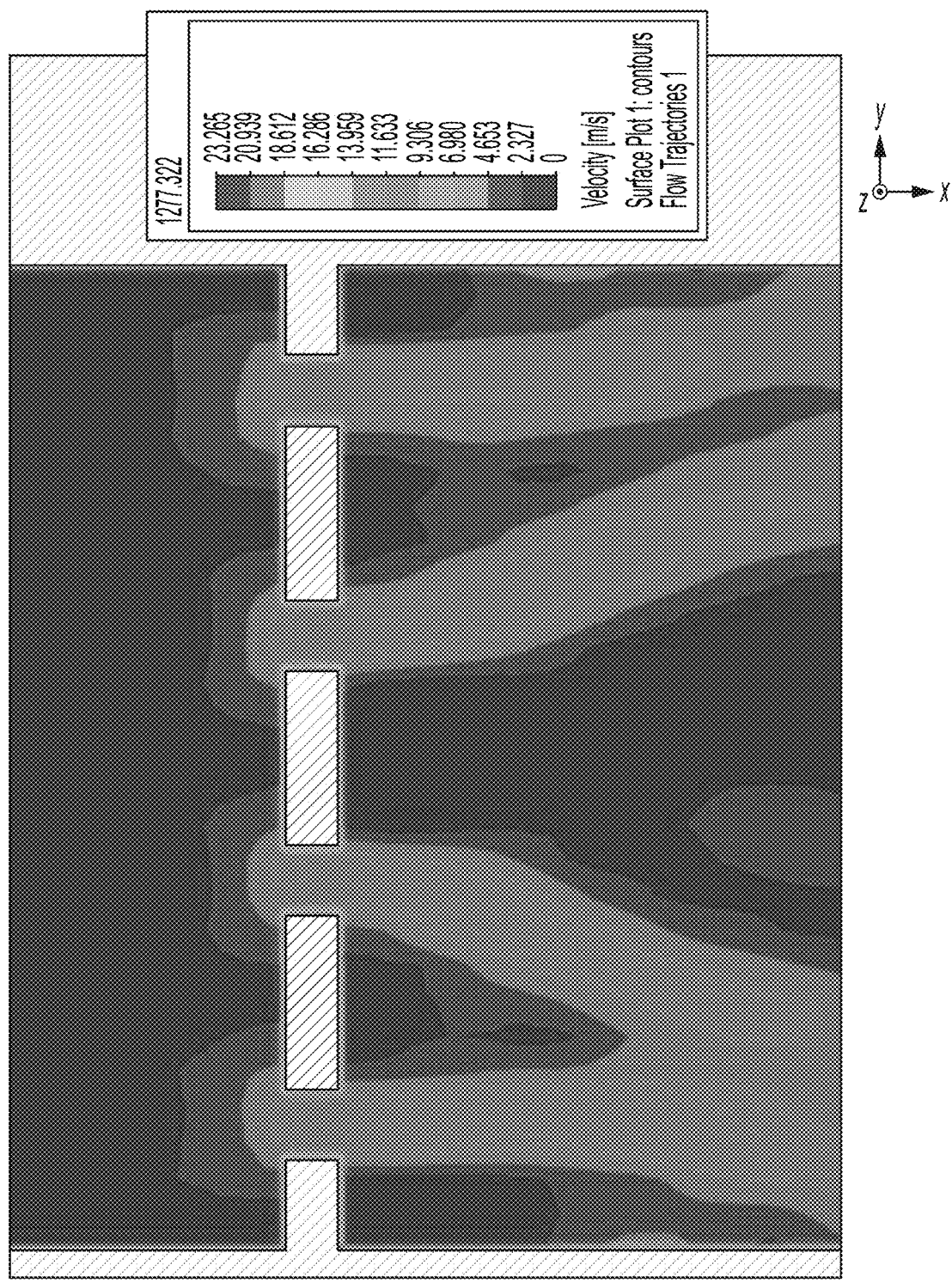

FIGS. 6A-6C illustrate flow velocities of various cell suspensions through chip embodiments similar to those shown in FIGS. 5A-5C. In FIGS. 6A-6C, the ten colors spanning the color gradient from royal blue to red, as shown in the color key in FIG. 6A, represent flow velocities spanning from (a) a lower end of between 0 m/s and 2.327 m/s to (b) an upper end of between 20.939 m/s and 23.265 m/s. As shown by the gradients, flow velocities are higher in and around the constrictions. In some embodiments, it may be desirable to configure chip geometries such that zones at which fluid slows and/or stagnates are minimized (in size and/or quantity) and/or eliminated. The chip embodiments in FIGS. 6A-6B have approach regions defined by different respective angles, and, in the case of FIG. 6C, the embodiment does not have angled approach regions adjacent the constrictions. The embodiment in FIG. 6A has approach regions with sidewalls that form a 40° angle with their respective opposite sidewalls; FIG. 6B shows a 60° angle embodiment; and FIG. 6C does not include any tapered or angled approach regions, similar to as shown in FIGS. 3A-3C (this may be referred to as a "180° angle embodiment").

In some embodiments, chip 100 may be configured to ensure sufficiently uniform flow velocity and flow patterns as the cell suspension approaches and flows through the plurality of constrictions. In some embodiments, the placement of inlet port 102 with respect to the set of parallelized constrictions 106 may help to ensure uniform flow velocity and flow patterns. Chip 100 may be configured such that inlet port 102 is spaced sufficiently far apart (e.g., in the x-direction) from the barrier (e.g., the line or curve) formed by the set of parallelized constrictions 106, relative to the lateral (e.g., y-direction) extent of the barrier.

In some embodiments, the plurality of constrictions may be arranged in a line forming a barrier or wall between a first flow region upstream of the parallelized plurality of constrictions and a second flow region downstream of the parallelized plurality of constrictions. The barrier formed by the plurality of constrictions may be located at a sufficient distance from an inlet port of the chip and a length of the barrier may be sufficiently short in relation to said distance that the flow velocity and flow patters through the plurality of constrictions are sufficiently uniform to maintain high throughput and low clogging.

In some embodiments, inlet port 102 may be spaced apart from the set of parallelized constrictions by a minimum spacing distance (e.g., a length of the shortest straight line between inlet port 102 and any point on the set of parallelized constrictions) of greater than or equal to 1 mm, 2.5 mm, 5 mm, 10 mm 15 mm, 20 mm, or 30 mm. In some embodiments, inlet port 102 may be spaced apart from the set of parallelized constrictions by a minimum spacing distance of less than or equal to 1 mm, 2.5 mm, 5 mm, 10 mm 15 mm, 20 mm, or 30 mm.

In some embodiments, the ratio of a distance from inlet port 102 to a nearest point on the boundary to a length of the boundary is greater than or equal to 0.0001, 0.005, 0.001, 0.01, 0.5, 0.1, 1, 10, 50, 100, or 250. In some embodiments, the ratio of a distance from inlet port 102 to a nearest point on the boundary to a length of the boundary is less than or equal to 0.0001, 0.005, 0.001, 0.01, 0.5, 0.1, 1, 10, 50, 100, or 250.

In some embodiments, the ratio of a distance to farthest point on the boundary from inlet port 106 to a distance to a nearest point of the boundary from inlet port 106 is less than or equal to 5, 2.5 2.25, 2, 1.75, 1.5, 1.25, 1.1, 1.05, 1.01, or 1.001. In some embodiments, the ratio of a distance to farthest point on the boundary from inlet port 106 to a distance to a nearest point of the boundary from inlet port 106 is greater than or equal to 5, 2.5 2.25, 2, 1.75, 1.5, 1.25, 1.1, 1.05, 1.01, or 1.001. In some embodiments, the ratio of a distance to farthest point on the boundary from inlet port 106 to a distance to a nearest point of the boundary from inlet port 106 is equal to 1.

In some embodiments, chips characterized by the ratios above may demonstrate superior flow uniformity, throughput, and clogging resistance.

Chip Embodiment Having Multiple Sets of Parallelized Constrictions

Figure 7:
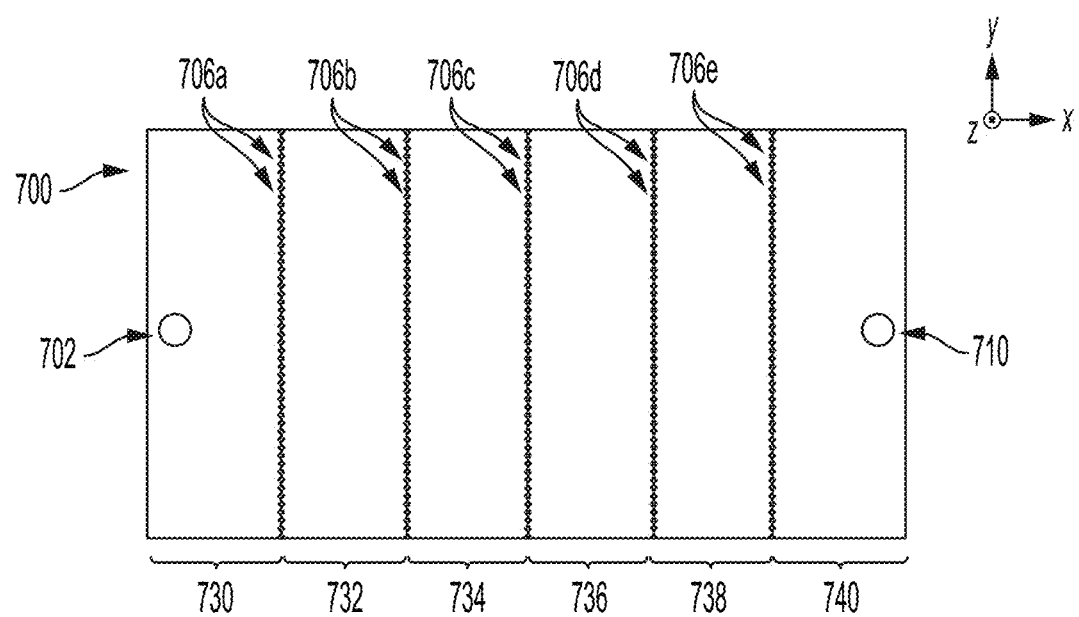
FIG. 7 illustrates a chip for delivering a payload to a cell, wherein the chip has multiple sets of parallelized constrictions and wherein the sets are in series with one another, in accordance with some embodiments.

FIG. 7 illustrates a chip for delivering a payload to a cell, wherein the chip has multiple sets of parallelized constrictions and wherein the sets are in series with one another, in accordance with some embodiments. FIG. 7 may share one or more characteristics in common with chip 100 described above with reference to FIGS. 1A-1C, including that chip 700 may be configured to guide the flow of fluid (e.g., cell suspension) from inlet port 702 to outlet port 710 through a plurality of cell-deforming constrictions forming a fluid path between the ports.

However, while chip 100 includes a single set of constrictions 706 provided in parallel to one another that form fluid flow paths between first fluid flow region 104 and second fluid flow region 108, chip 700 may comprise multiple sets of fluidly parallelized constrictions. As shown in FIG. 7, chip 700 may include a first set of constrictions 706a, a second set of constrictions 706b, a third set of constrictions 706c, a fourth set of constrictions 706d, and a fifth set of constrictions 706e. The constrictions within each one of the individual sets 706a-706e may be positioned in parallel with one another, like the set of parallelized constrictions 106 in chip 100, providing fluidly parallelized flow paths from an upstream fluid flow region to a downstream fluid flow region. However, the sets themselves of parallelized constrictions 706a-706b may be provided in series with one another, such that the fluid flow paths provided by a first set (e.g., 706a) may be upstream of the fluid flow paths provided by a second flow path (e.g., 706b). In chip 700, fluid flowing from inlet port 702 to outlet port 710 may traverse first fluid flow region 730, second fluid flow region 732, third fluid flow region 734, fourth fluid flow region 736, fifth fluid flow region 738, and finally sixth fluid flow region 740, which may be arranged in series with one another and may be separated by the sets of constrictions 706 as shown.

In some embodiments, adjacent sets of constrictions (e.g., 706a and 706b) may be offset from one another in the flow direction (e.g., in the x-direction in FIG. 7) by less than or equal to 25 µm, 50 µm, 100 µm, 500 µm, 1 mm, 1 cm, or 5 cm. In some embodiments, adjacent sets of constrictions (e.g., 706a and 706b) may be offset from one another in the flow direction (e.g., in the x-direction in FIG. 7) by greater than or equal to 25 µm, 50 µm, 100 µm, 500 µm, 1 mm, 1 cm, or 5 cm.

While the example of FIG. 7 shows chip 700 with five separate sets of parallelized constrictions, a chip may be provided with any suitable number of sets of parallelized constrictions. For example, a chip may have 2, 3, 4, 5 or more, 10 or more, or 20 or more sets of parallelized constrictions provided in series.

Figure 8:
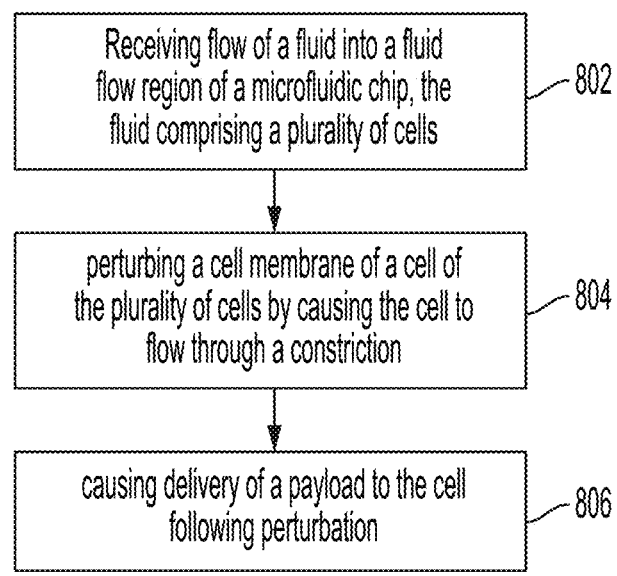
FIG. 8 illustrates a method of causing the delivery of a payload to a cell, according to some embodiments.

Method of Delivery of a Payload to a Cell Using a Microfluidic Chip Described Herein FIG. 8 illustrates a method of causing the delivery of a payload to a cell, according to some embodiments. The method of FIG. 8 may be performed using one or more chips having parallelized constrictions as described herein, such as (but not limited to) chip 100 of FIGS. 1A-1C or chip 700 of FIG. 7. FIG. 8 is described below with exemplary reference to chip 100

At step 802, the microfluidic chip (e.g., microfluidic chip 102 of FIG. 1) receives flow of a fluid into a first fluid flow region. The fluid, such as a cell suspension, comprises a plurality of cells. In some embodiments, the fluid can also include a payload to be delivered into one or more of the cells in the fluid. Specifically, the microfluidic chip receives flow of a fluid in a first fluid flow region that is upstream of a set of parallelized constrictions that fluidly connect the first fluid flow region to a second fluid flow region downstream of said set of parallelized constrictions.

At step 804, the microfluidic chip (e.g., microfluidic chip 102 of FIG. 1) causes perturbation of a cell membrane of a cell from the fluid by causing the cell to flow through the set of parallelized constrictions in the microfluidic chip. As described herein, the set of constrictions may be formed by etching channels into a substrate of the chip and may be configured to guide cell suspension toward and through the constrictions.

At step 806, delivery of a payload to the perturbed cell is caused. Payload delivery may occur in the second fluid flow region, downstream of the set of parallelized constrictions, after passage of the cell suspension through the constrictions and perturbation of the cell membranes caused thereby. In some embodiments, the payload is introduced to the cell suspension following perturbation, at the second fluid flow region and/or in a fluid vessel or reservoir separate from chip 100. After delivery of the payload, the cell membrane may heal.

In some embodiments, cells processed through one or more constrictions of a microfluidic chip described herein, for example in accordance with method 800, may demonstrate a viability percentage following passage through the constriction(s) of greater than or equal to 30%, 50%, 70%, 90%, 95% or 99%.

In some embodiments, cells processed through one or more constrictions of a microfluidic chip described herein, for example in accordance with method 800 may demonstrate a payload delivery percentage of greater than or equal to 30%, 50%, 70%, 90%, 95% or 99%.

Chips Disposed in a Cartridge

Figure 9:
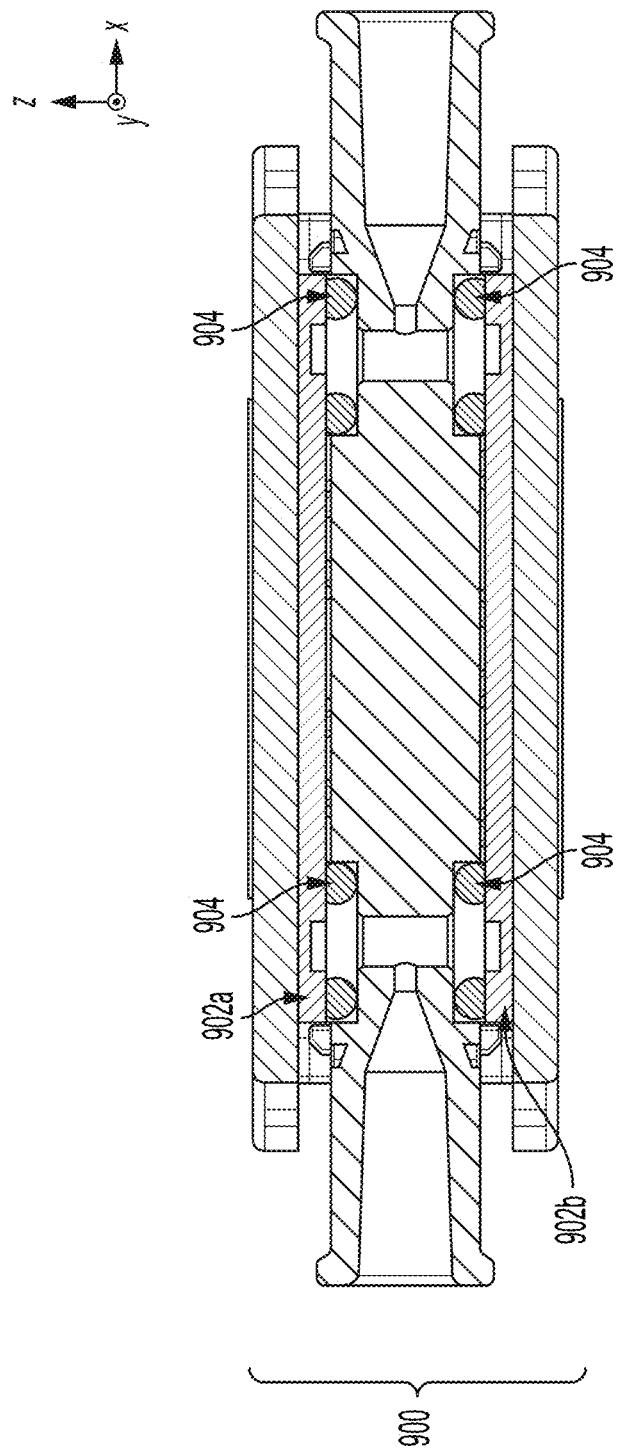
FIG. 9 shows a cartridge holding chips for delivering a payload to a cell, in accordance with some embodiments.

FIG. 9 shows cartridge 900 holding two chips 902a and 902b therein. Cartridge 900 may hold chips inside it and direct the flow of fluid to and from chips held therein. As shown by the cross-sectional view of FIG. 9, o-rings 904 may press against a chip and surround an inlet or outlet port of the chip, holding the chip in place and forming a seal around the inlet/outlet port and facilitating flow of fluid into or out of the chip without leaking.

Fluid Flow Region Geometries

Figure 10A:
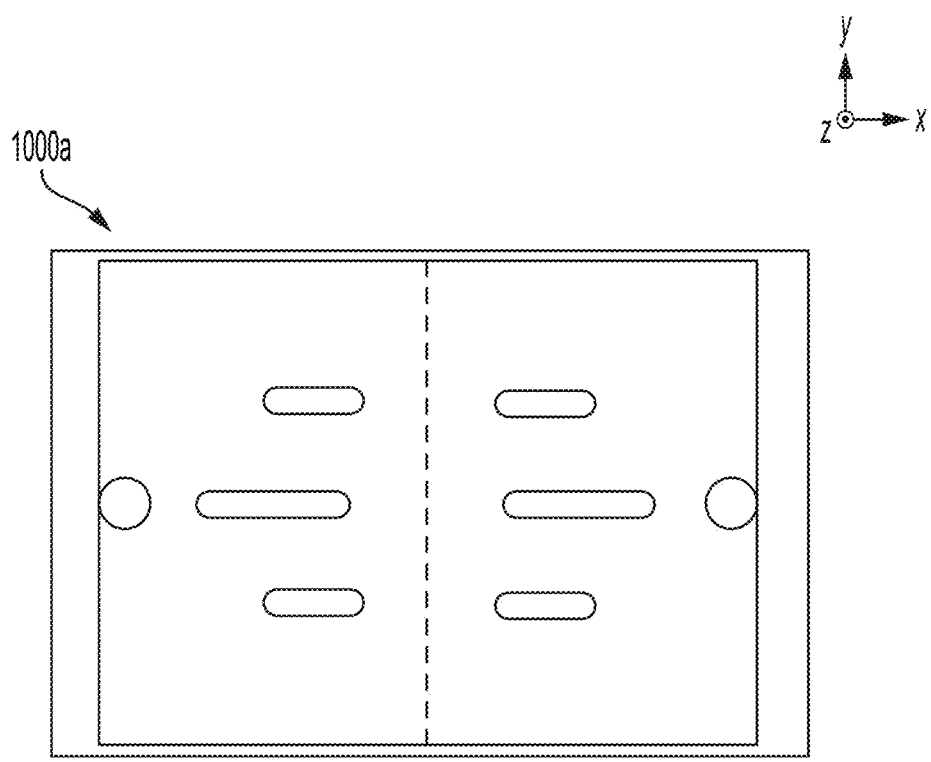
FIGS. 10A-10C show various chips for delivering a payload to a cell, wherein the chip have fluid flow regions having various geometries.
Figure 10B:
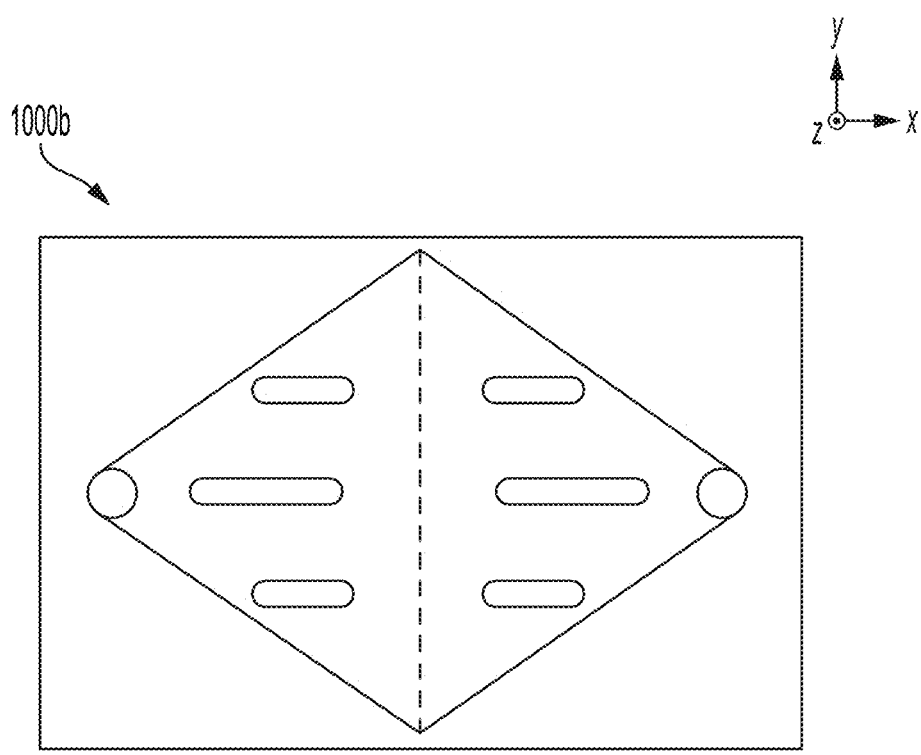
Figure 10C:
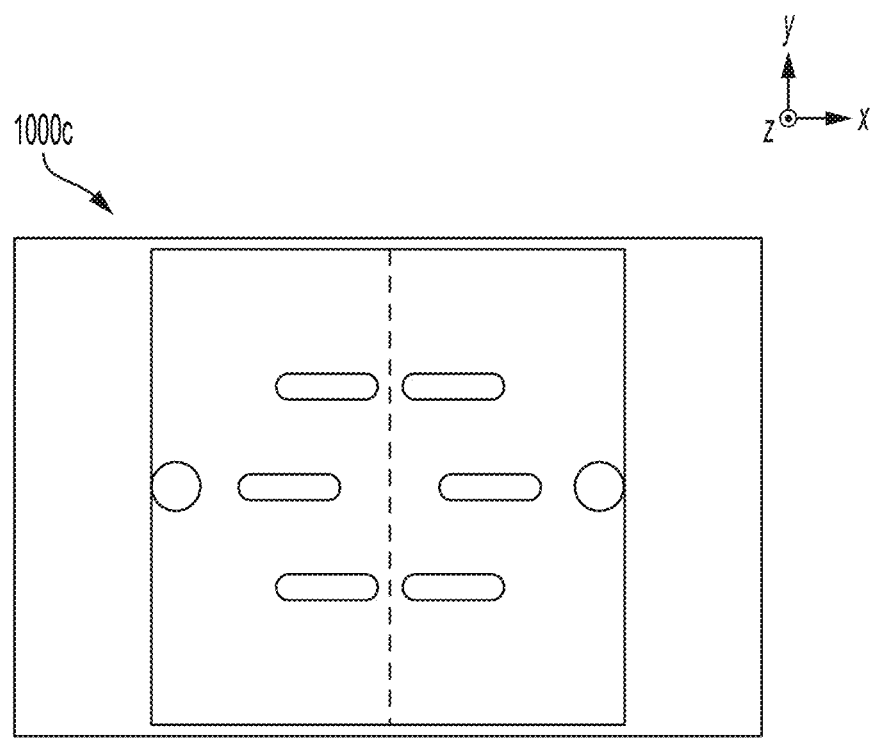

FIGS. 10A-10C show chips having various fluid flow region geometries. Specifically, while chip 100 shown in FIGS. 1A-1C has fluid flow regions that are shaped as irregular pentagons (in an overhead view of an x-y plane), the cartridges in FIGS. 10A-10C may have fluid flow regions of other shapes.

Cartridge 1000a shown in FIG. 10A has fluid flow regions shaped as rectangles; cartridge 1000b shown in FIG. 10B has fluid flow regions shaped as triangles; and cartridge 1000c shown in FIG. 10C has fluid flow regions shaped as rectangles that together form a square.

Example 1

Performance of different chips was compared, where constrictions of a first set of two chips in parallel were 4 µm in width, and constrictions of a second set of two chips in parallel were 4.5 μm in width. Each chip contained 75 constrictions arranged in parallel. For all chips, constriction length was 10 μm. For all chips, a pressure of 50 PSI and a temperature of 2-8° C. was used. For all chips, the blood product Hemacare LP was used at a concentration of 7.20× 10$^7$ cells/mL. For all chips, a delivery media of RPMI and a delivery material of 0.01 mg·ML 3 kDa Dextran AF 680 was used.

Performance of the chips is shown in Table 1 below:

TABLE 1

| Chip Constriction Width | NucleoCounter® NC-200™ Viability Post-Squeeze at T0 | Live Cell Recovery Through 2 hour Incubation | Total Live Cells Passed through chips |
|---|---|---|---|
| 4 μm | 72.4% | 43.6% | 2.88e9 |
| 4.5 μm | 79.6% | 64.5% | 3.96e9 |

Example 2

Performance of a chip having 75 constrictions arranged in parallel, each constriction having a width of 4 μm and etch depth of 66 μm was tested. The chip performed a microfluidic squeeze under the following pressures: 40 PSI, 50 PSI, and 60 PSI. These three runs or "squeezes" were plotted against three control squeezes: Control 1 (chip with constrictions measuring 30 μm length, 4 μm width, and 20 μm depth tested at 60 PSI), Control 2 (addition of dextran to cell suspension with no microfluidic squeezing), Control 3: (no addition of dextran and no microfluidic squeezing), to show the percentage of live B cells, percentage of dextran delivery, and relative mean fluorescence intensity as shown in FIG. 11.

Figure 11:
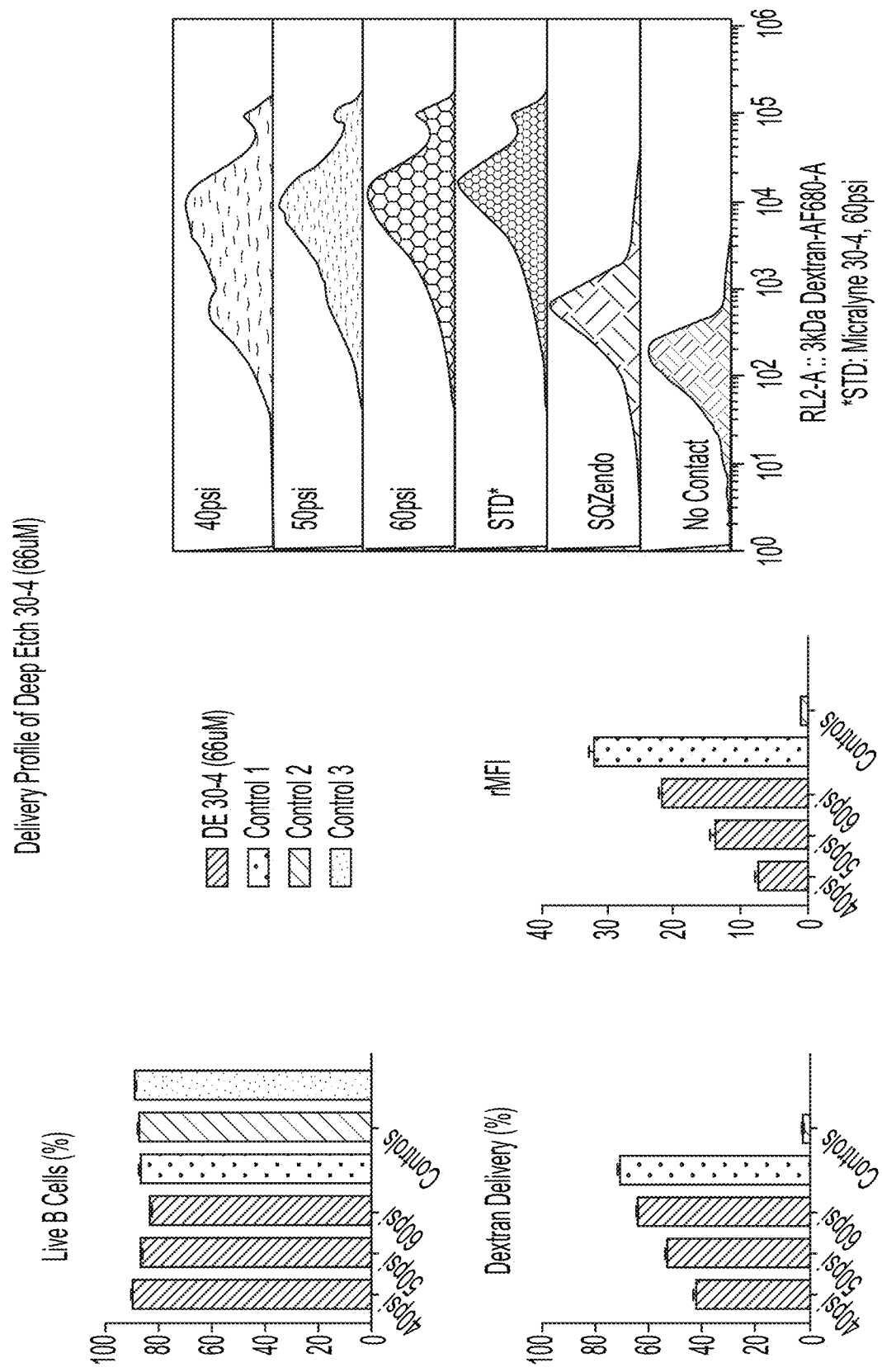
FIG. 11 shows experimental delivery profile data for a chip for delivering a payload to a cell, in accordance with some embodiments.

The graphs on the right in FIG. 11 are histograms showing fluorescence analysis of the uptake of dextran by cells under different conditions. The top three histograms represent squeezes under different pressures: 40 PSI, 50 PSI, and 60 PSI. "STD" represents squeeze conditions with a chip with constrictions measuring 30 μm length, 4 μm width, and 20 μm depth tested at 60 PSI. "SQZendo" represents the delivery of dextran by only contacting the cells with dextran but without squeezing and shows uptake of dextran into the cells by endocytosis. "No contact" represents the fluorescence of the cells without dextran and no squeezing was performed.

Performance of a chip having 75 constrictions arranged in parallel, each constriction having a width of 4 μm and etch depth of 97 μm was tested. The chip performed a microfluidic squeeze under the following pressures: 15 PSI, 30 PSI, 45 PSI, and 60 PSI. These four squeezes were plotted against three control squeezes: Control 1 (chip with constrictions measuring 30 μm length, 4 μm width, and 20 μm depth tested at 60 PSI), Control 2 (addition of dextran to cell suspension with no microfluidic squeezing), Control 3: (no addition of dextran and no microfluidic squeezing), to show the percentage of live B cells, percentage of dextran delivery, and relative mean fluorescence intensity as shown in FIG. 12.

Figure 12:
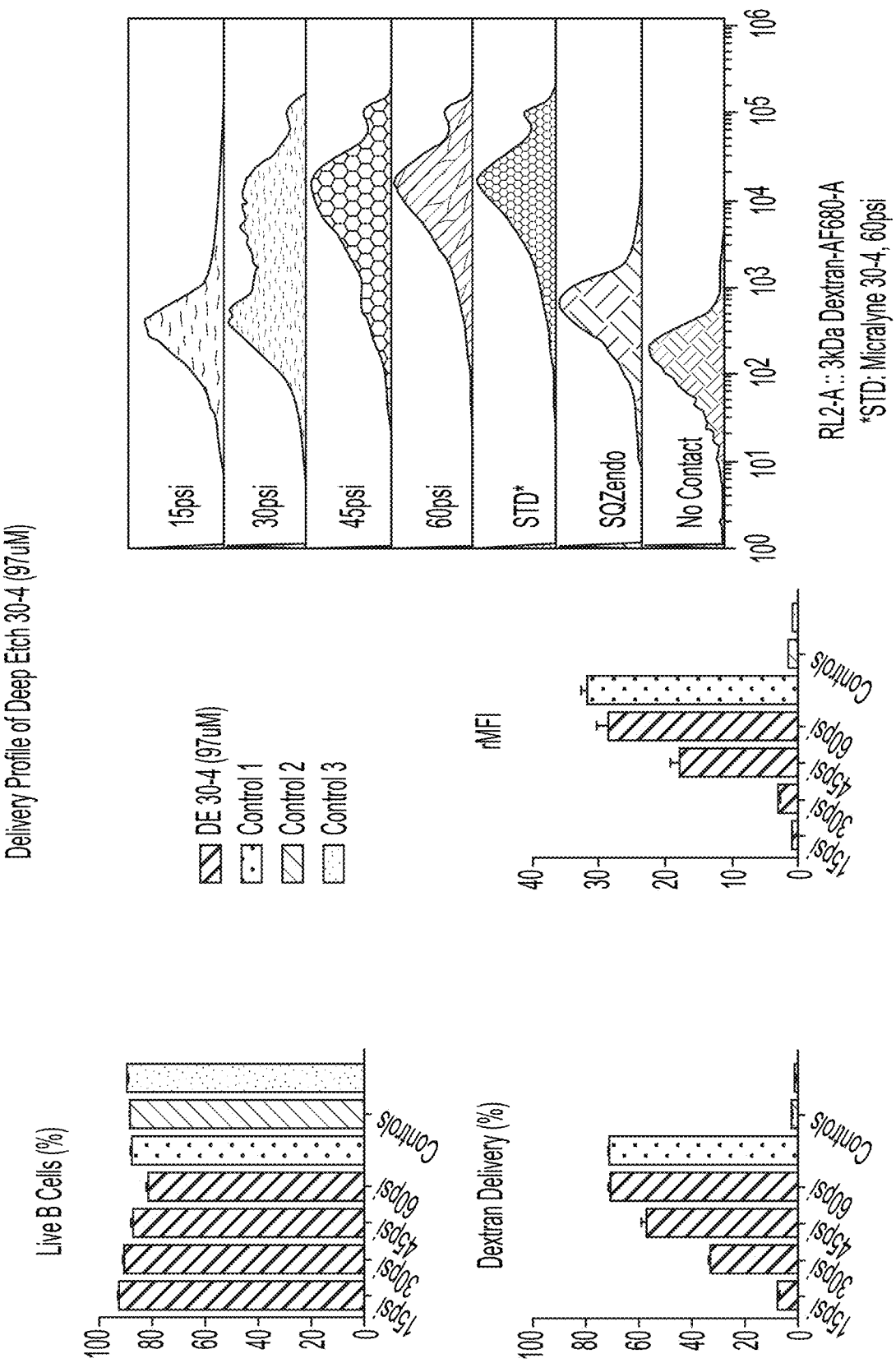
FIG. 12 shows experimental delivery profile data for a chip for delivering a payload to a cell, in accordance with some embodiments

The graphs on the right in FIG. 12 are histograms showing fluorescence analysis of the uptake of dextran by cells under different conditions. The top four histograms represent squeezes under different pressures: 15 PSI, 30 PSI, 45 PSI, and 60 PSI. "STD" represents squeeze conditions with a chip with constrictions measuring 30 μm length, 4 μm width, and 20 μm depth tested at 60 PSI. "SQZendo" represents the delivery of dextran by only contacting the cells with dextran but without squeezing and shows uptake of dextran into the cells by endocytosis. "No contact" represents the fluorescence of the cells without dextran and no squeezing was performed.

Example 3

A chip was fabricated having 950 constrictions arranged in parallel, each constriction having a width of 4.5 μm, a length of 10 μm, and a etch depth of 80 μm. The overall size of the chip was 30 mm in length, 20 mm in width, and 1225 μm in height (thickness). The chip included an inlet fluidic port spaced 24 mm from an outlet fluidic port, each port having a diameter of 2.00 mm. The chip included a silicon substrate of 600 μm in height (thickness) and a glass top layer of 600 μm in thickness.

Target constriction dimensions for fabricating the chip were 4.50±0.20 μm for constriction width, 10±1 μm for constriction length, and 80±2 μm for constriction height (depth).

Specifications for fabricating the chip were as shown in Table 2 below:

TABLE 2

| Specification | Target | Min | Max |
|---|---|---|---|
| Glass wafer thickness, μm | 625 | 600 | 650 |
| Silicon wafer thickness, μm | 600 | 575 | 625 |
| Total device thickness, μm | 1225 | 1175 | 1275 |
| Constriction width, μm | 4.50 | 4.30 | 4.70 |
| Variation in constriction width, μm | 0 | −0.20 | 0.20 |
| Constriction depth, μm | 80 | 72 | 88 |
| Constriction angle, ° | 22 | 20 | 24 |
| Constriction length, μm | 10 | 9 | 11 |
| Number of constrictions | 950 | N/A | N/A |
| Chip width, mm | 20.0 | 19.9 | 20.1 |
| Chip length, mm | 30.0 | 29.9 | 30.1 |
| Glass via diameter, mm | 2.00 | 1.95 | 2.05 |
| Silicon to glass misalignment, μm | 0.0 | −100 | 100 |

Constriction width was measured as the average constriction width of 10% of all of the constrictions on the chip, measured at the top of the constrictions.

Variation in constriction width was measured within a given constriction, measured based on SEM cross section of select chips across a wafer.

The chip fabrication process was configured such that 80% of chips manufactured thereby were expected to be within the specifications set out in Table 2.

Example 4

Performance was tested for six chip types, each of the six chip types having multiple sets of constrictions arranged in parallel where the sets are in series. The six chip types are illustrated schematically in FIG. 13A.

Chip layout 5f has five sets of parallelized constrictions, the sets in series with one another and spaced apart from one another by a first spacing distance.

Chip layout 5c has five sets of parallelized constrictions, the sets in series with one another and spaced apart from one another by a second spacing distance that is less than the first spacing distance.

Chip layout 10 has ten sets of parallelized constrictions, the sets in series with one another and spaced apart from one another by the second spacing distance.

Chip type 1 has the "5f" chip layout with upstream approach regions angled at 20° and downstream approach regions angled at 45°.

Chip type 2 has the "5c" chip layout with upstream approach regions angled at 20° and downstream approach regions angled at 45°.

Chip type 3 has the "10" chip layout with upstream approach regions angled at 20° and downstream approach regions angled at 45°.

Chip type 4 has the "5f" chip layout with upstream approach regions angled at 20° and downstream approach regions angled at 60°.

Chip type 5 has the "5c" chip layout with upstream approach regions angled at 20° and downstream approach regions angled at 60°.

Chip type 6 has the "10" chip layout with upstream approach regions angled at 20° and downstream approach regions angled at 60°.

For each of the six chip types, the constrictions had length 10 μm, width 3 μm, and height (etch depth) 70 μm.

For each of the six chip types, 88 chips were tested. The six chips types were tested using different pressures and/or using blood from different donors. Furthermore, the chips were tested in various directions, e.g., by running the chips both "forward" and "backward." Results are indicated in FIGS. 13B-13H according to the angle of the approach region that was actually upstream in the run. That is, for runs labeled "45°" for Chip type 1, the chip was reversed such that the 45° approach regions were upstream and the 20° approach regions were downstream. Results are described below.

Figure 13A:
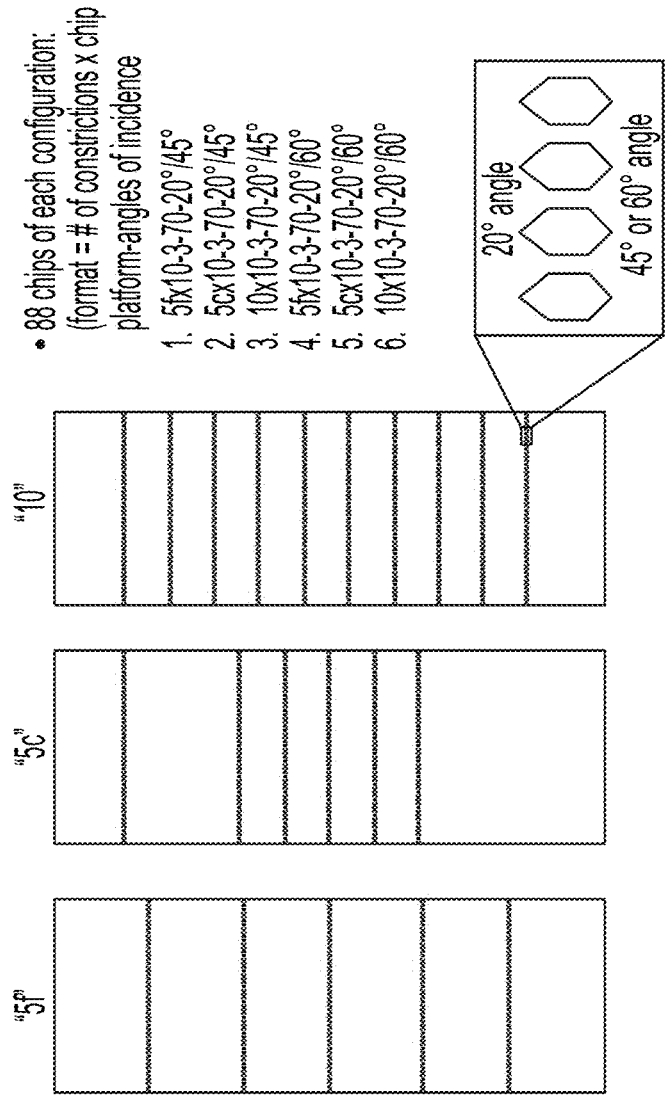
FIGS. 13A-13O show chip schematics information and experimental data from testing chips having sets of parallelized constrictions wherein the sets are in series with one another, in accordance with some embodiments.
Figure 13B:
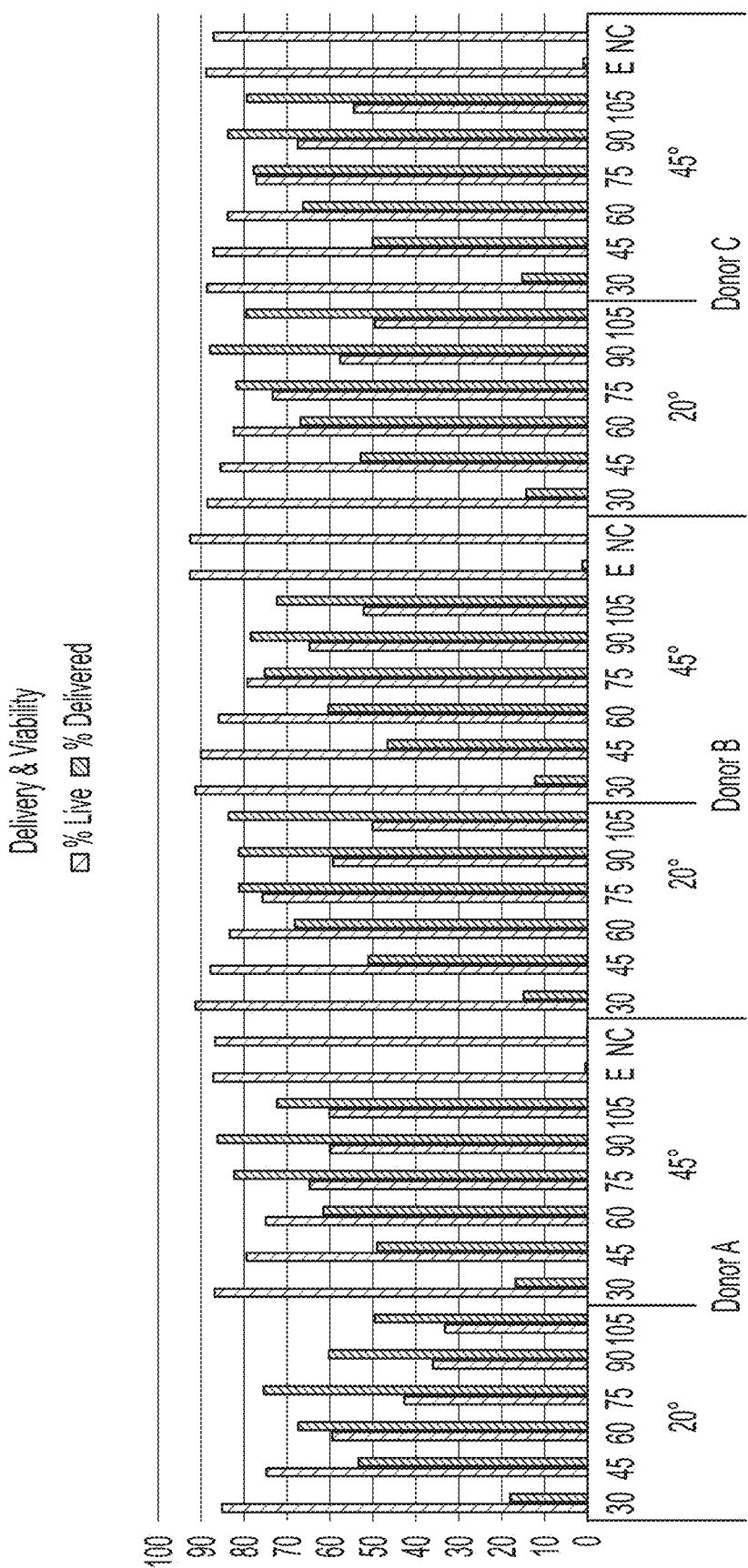

FIG. 13B shows viability percentage and delivery percentage results for tests of Chip type 1 at various pressures (30, 45, 60, 75, 90, and 105 PSI), in various orientations, and using blood from three different donors (A, B, and C).

Figure 13C:
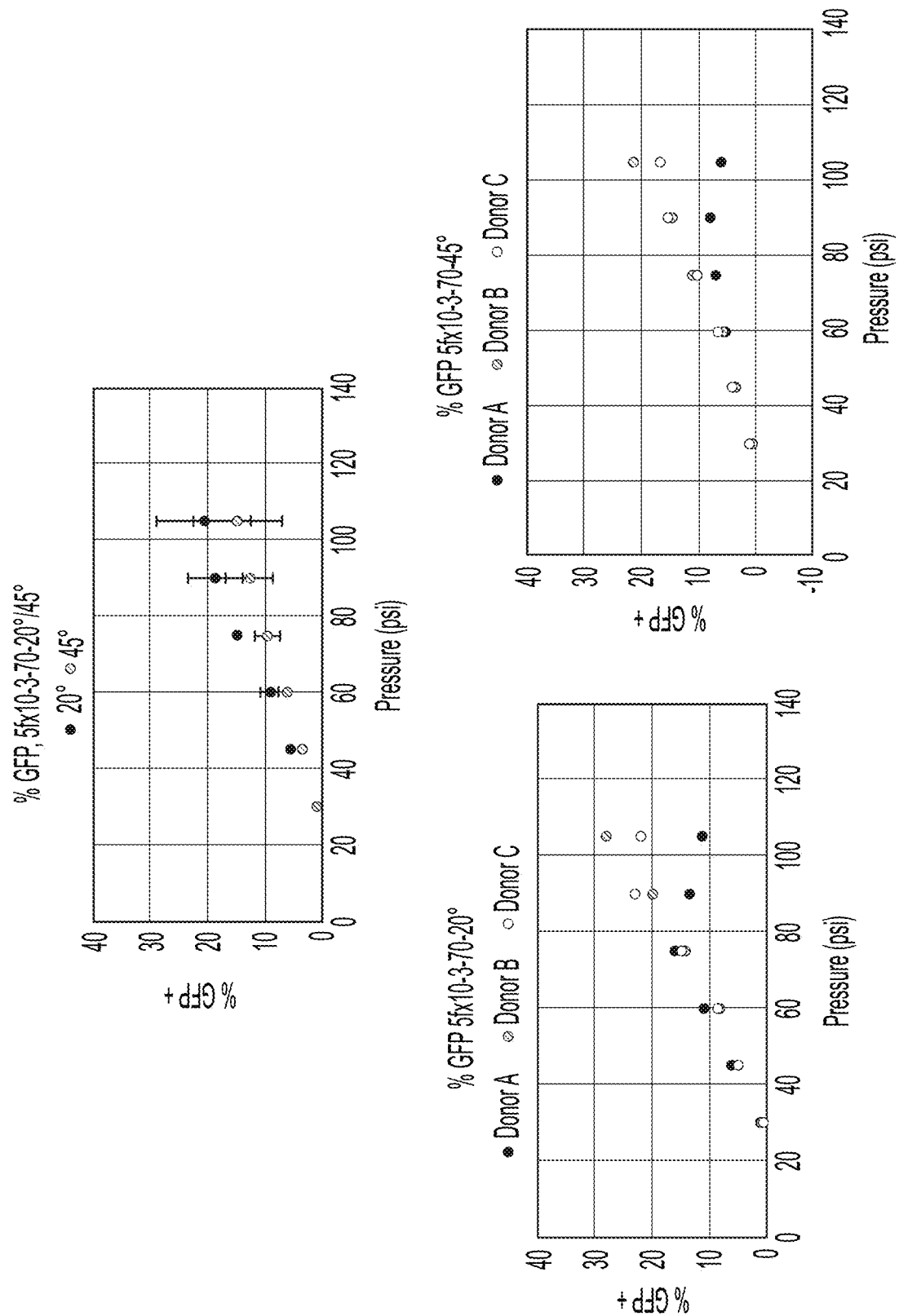

FIG. 13C shows detection of active GFP in the cells for tests of Chip type 1 at various pressures (30, 45, 60, 75, 90, and 105 PSI), in various orientations, and using blood from three different donors (A, B, and C).

Figure 13D:
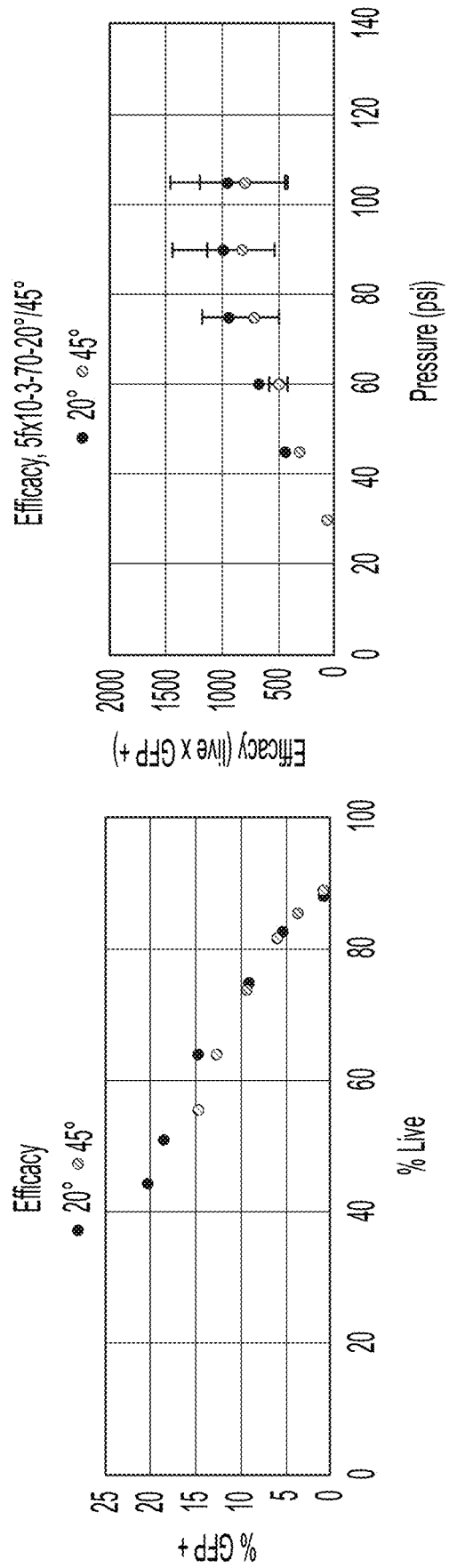
Figure 13E:
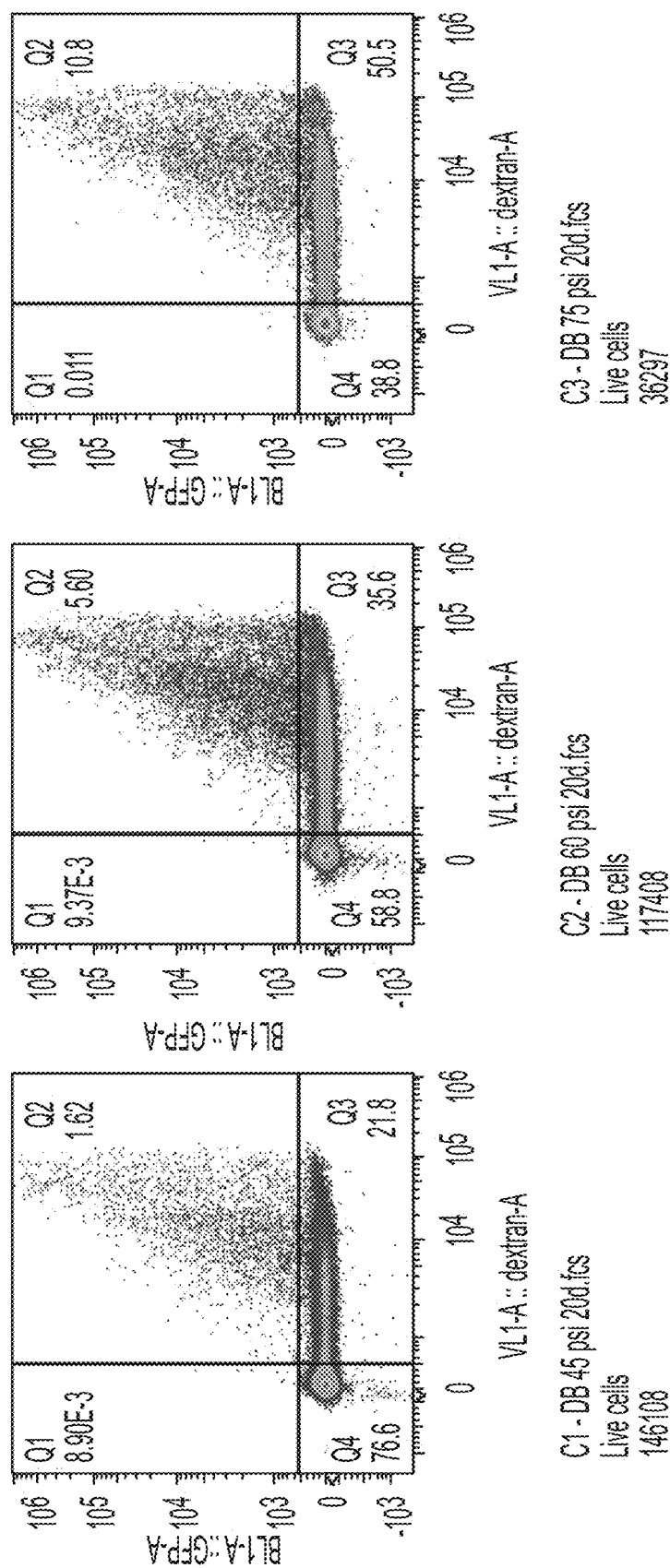
Figure 13F:
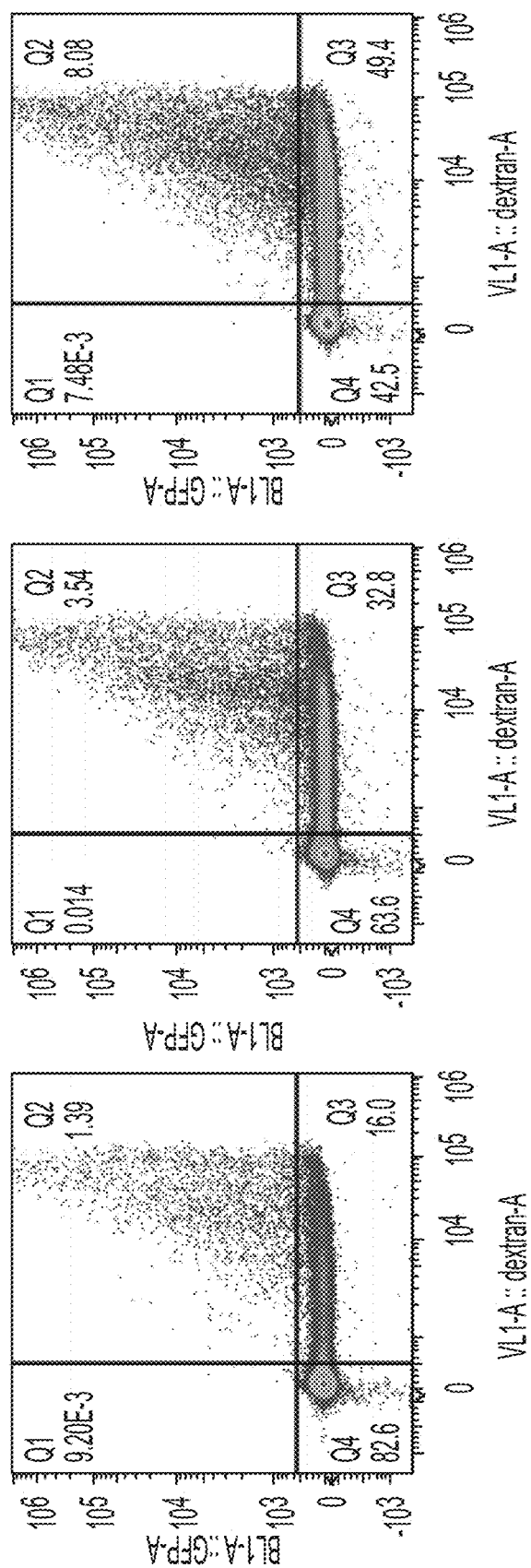
Figure 13G:
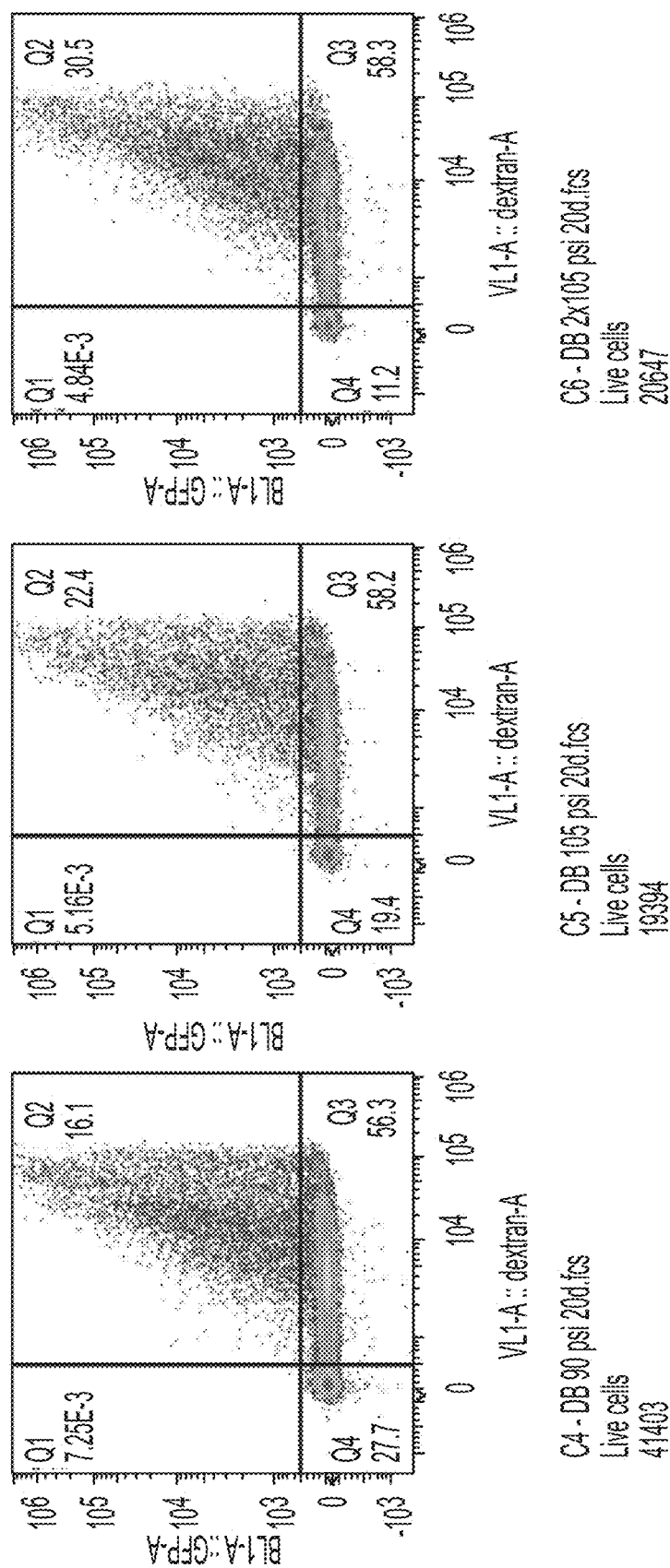
Figure 13H:
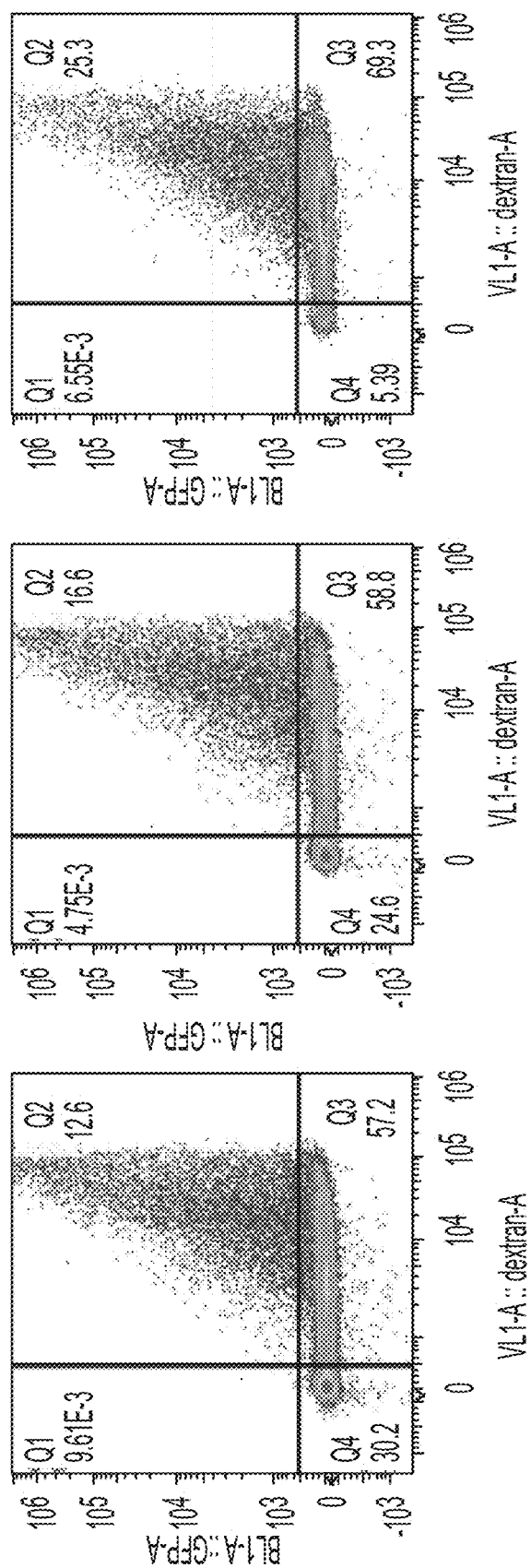

FIG. 13D shows efficacy results for tests of Chip type 1 at various pressures (30, 45, 60, 75, 90, and 105 PSI) and in various orientations.

FIGS. 13E-13H show FACS plots for tests of chip type 1. GFP fluorescence in cells is plotted against dextran fluorescence in cells.

Figure 13I:
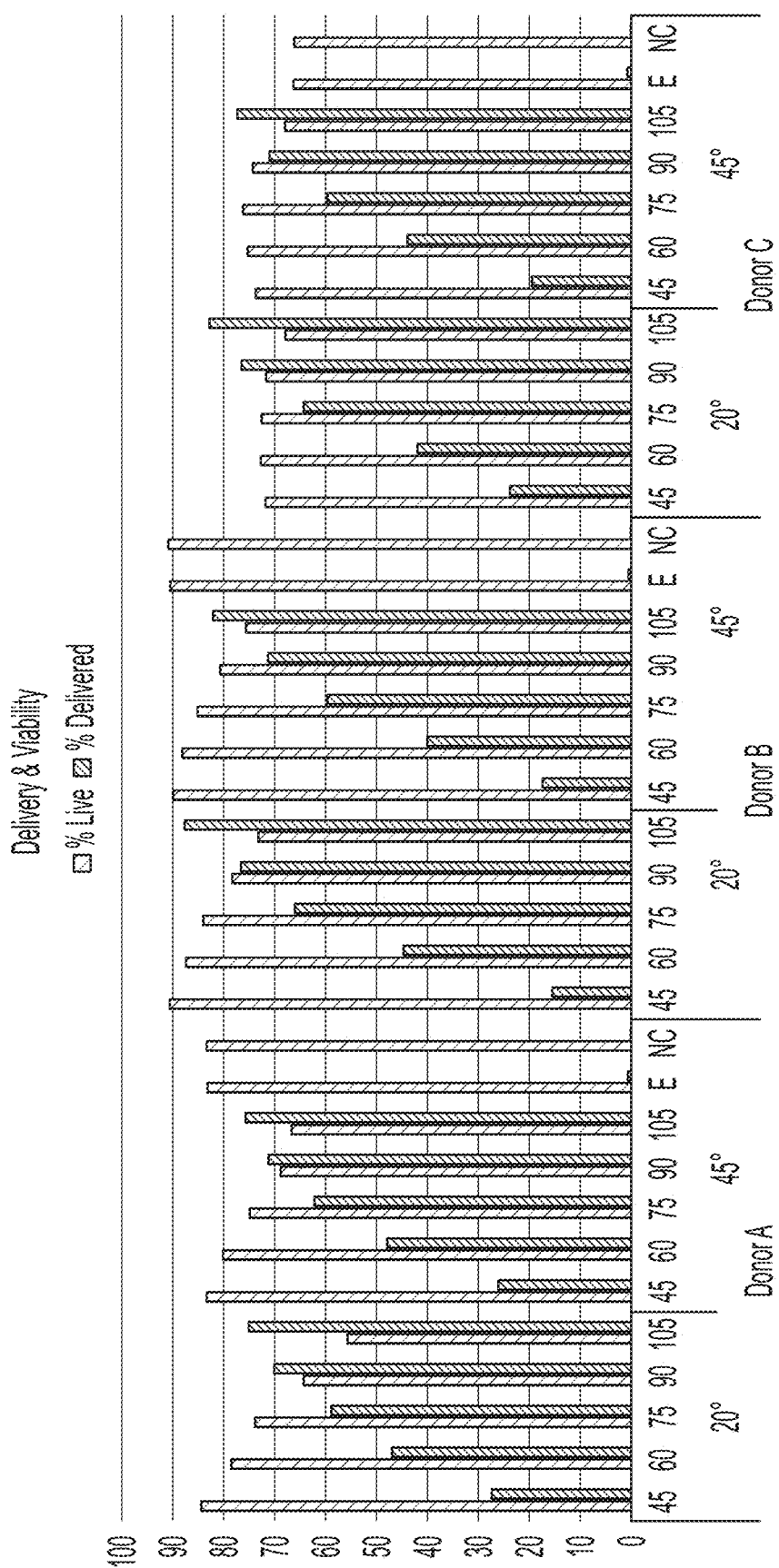

FIG. 13I shows viability percentage and delivery percentage results for tests of Chip type 3 at various pressures (45, 60, 75, 90, and 105 PSI), in various orientations, and using blood from three different donors (A, B, and C).

Figure 13J:
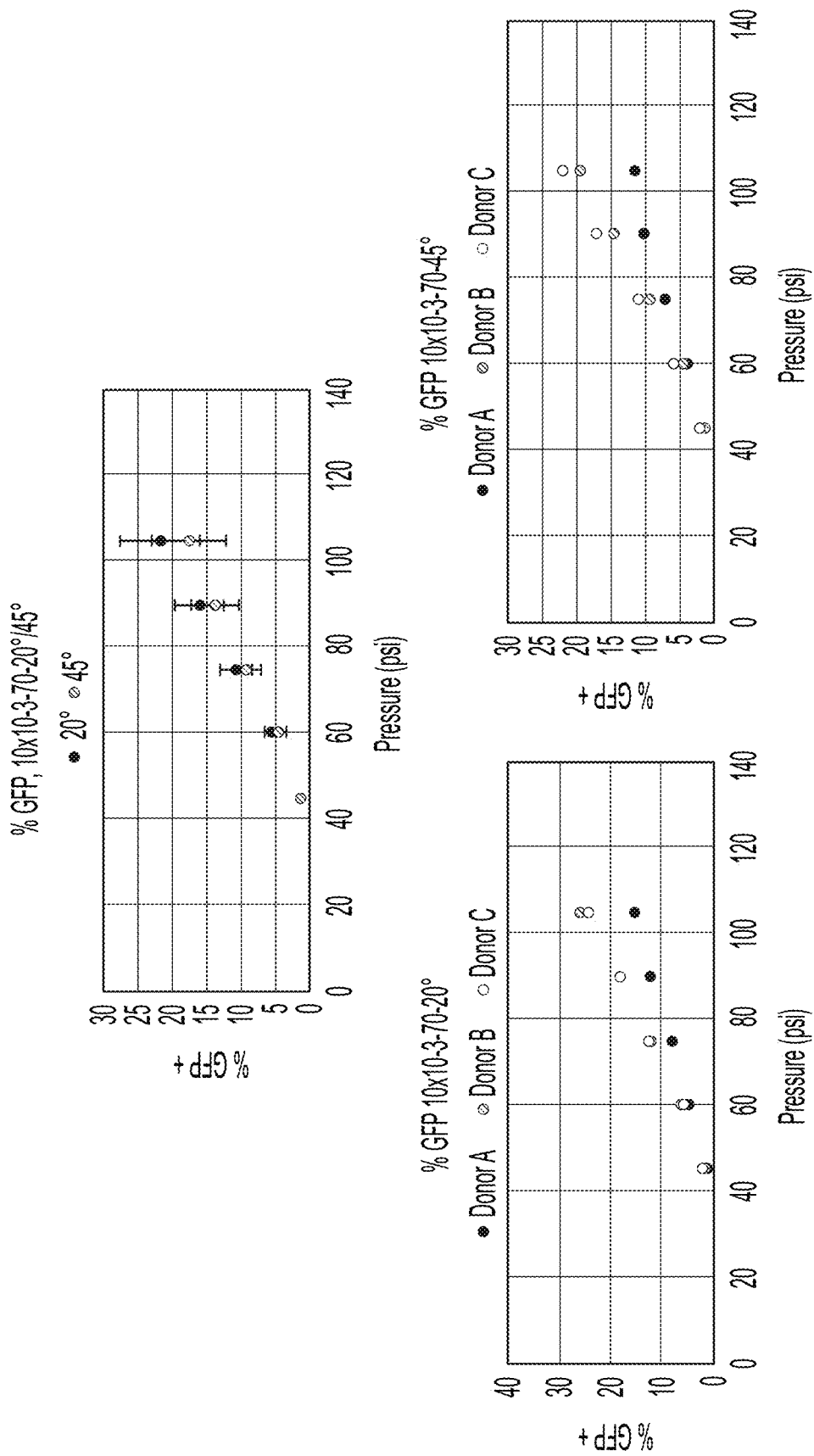
Figure 3K:
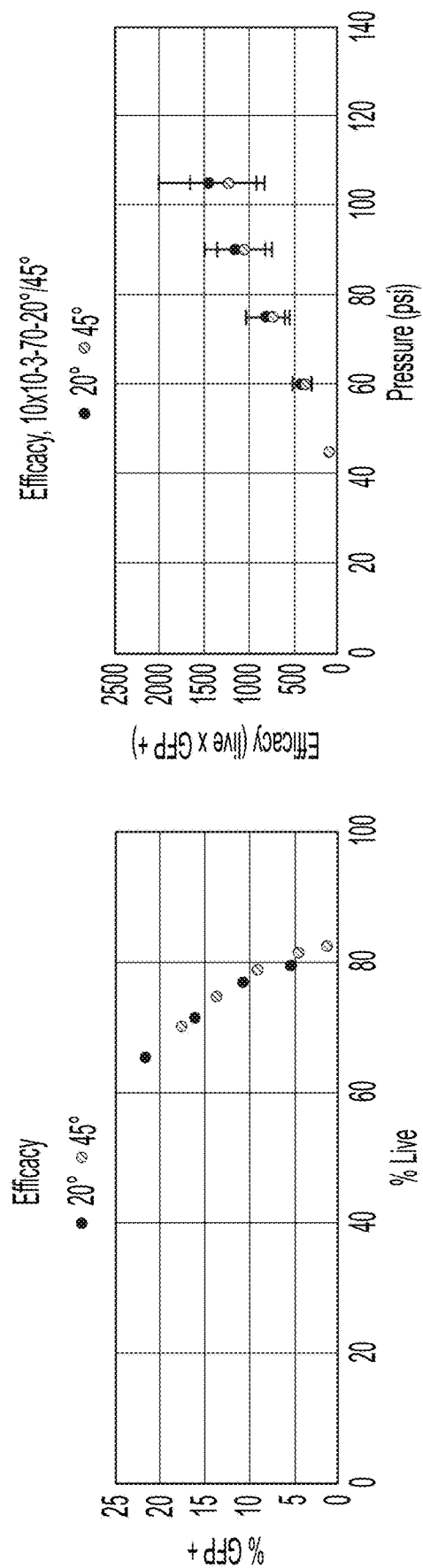
Figure 13L:
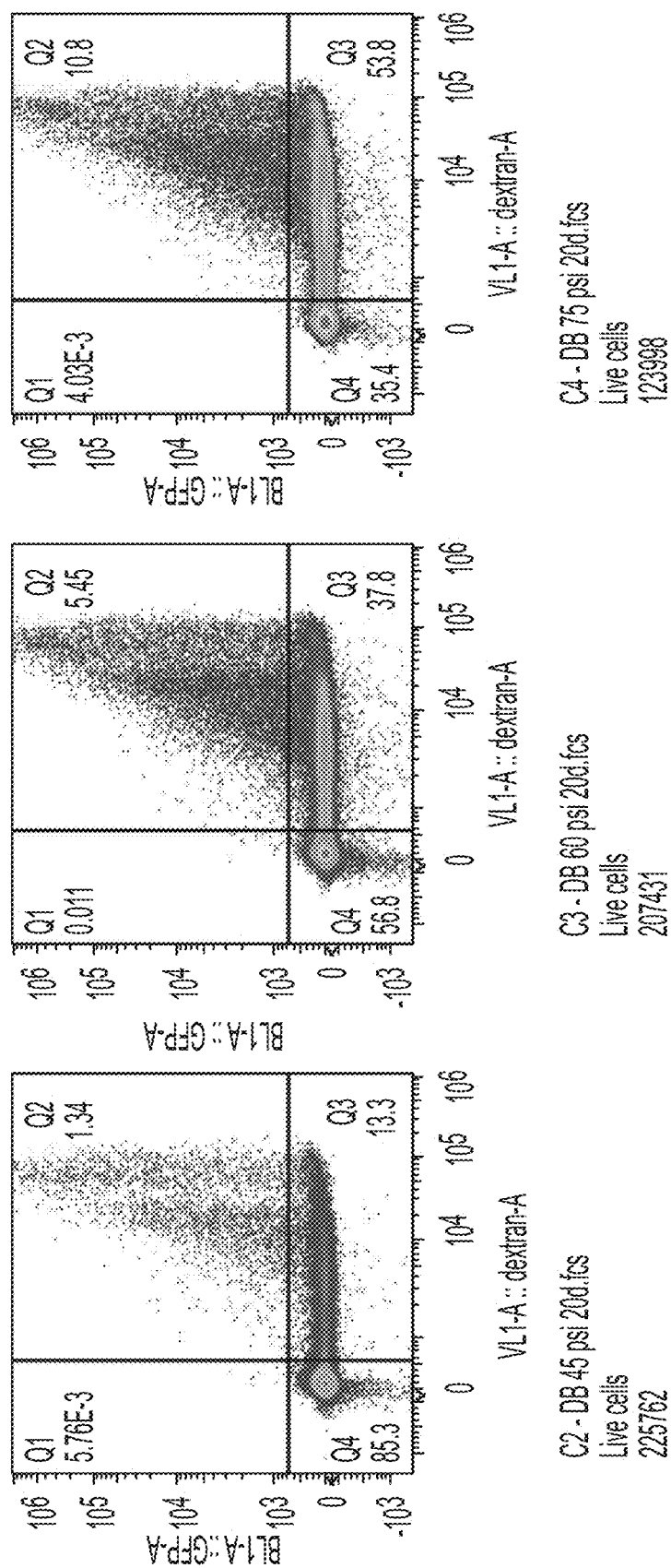
Figure 13M:
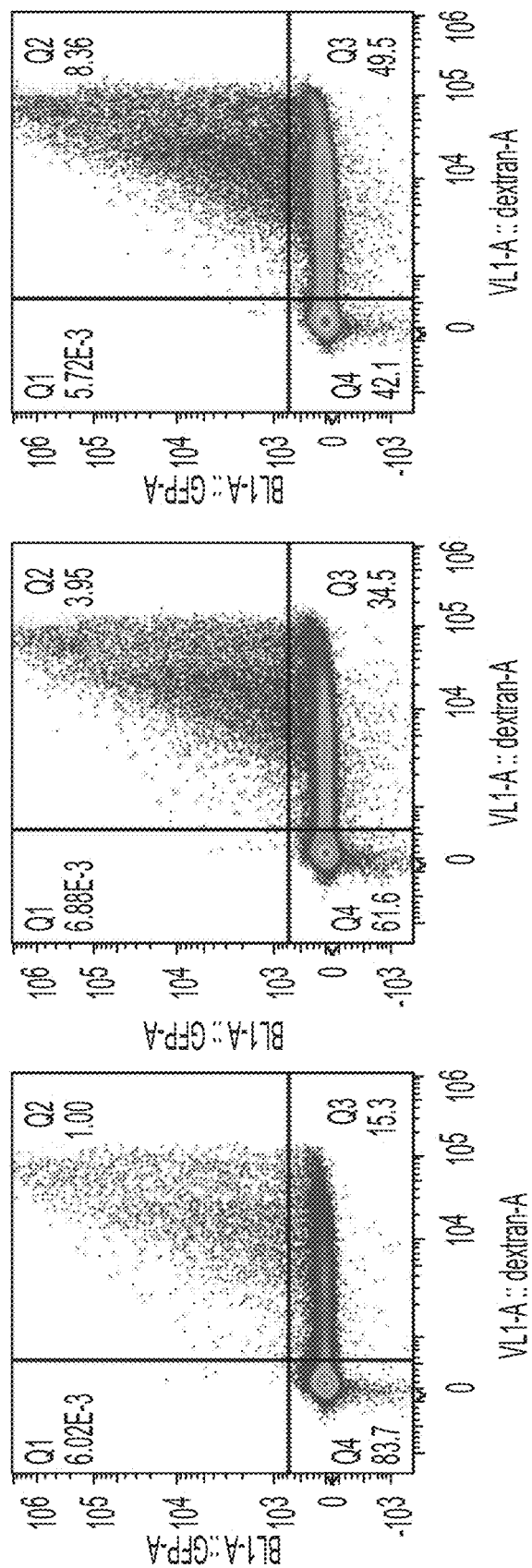
Figure 13N:
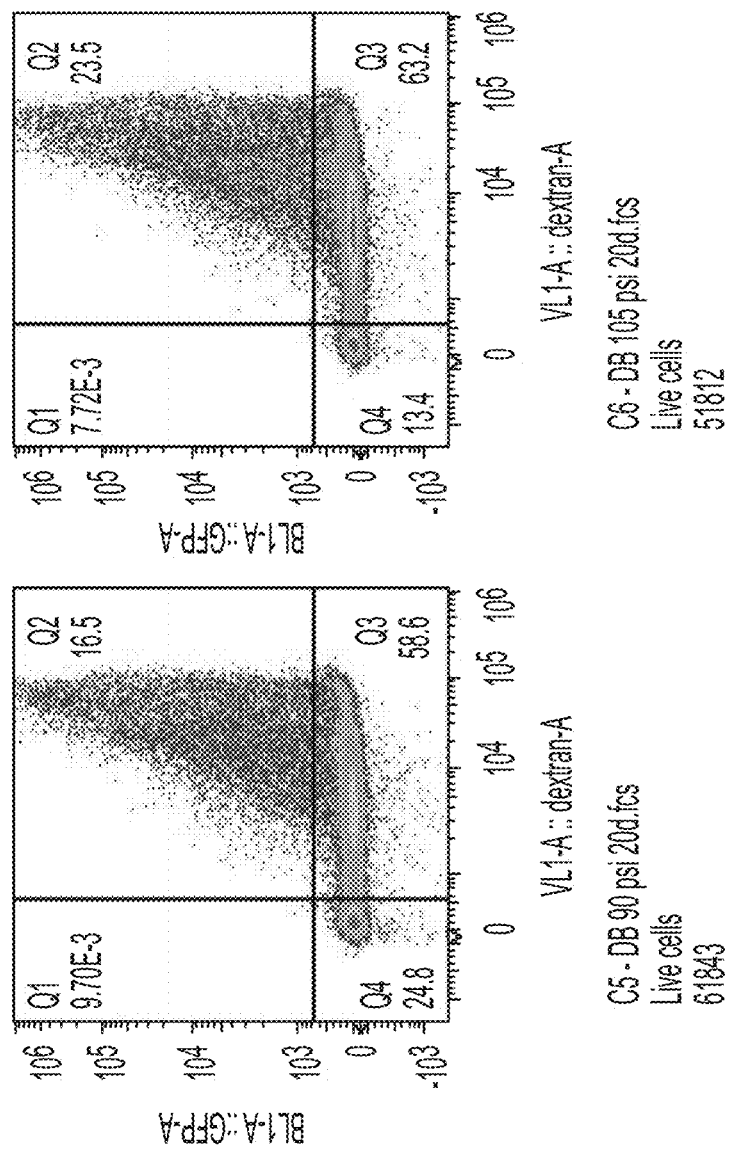
Figure 13O:
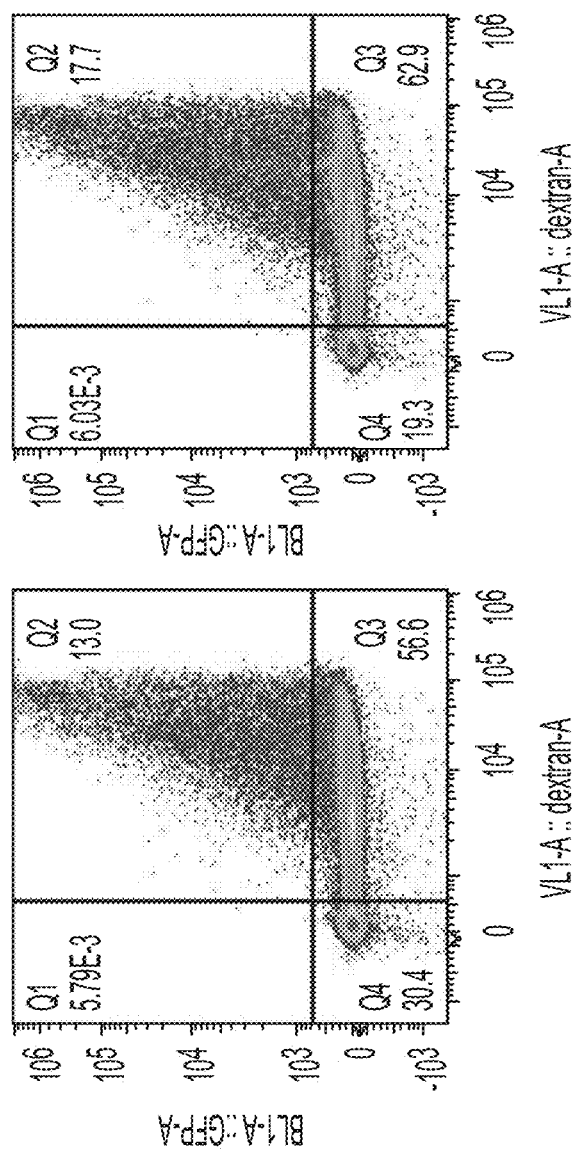

FIG. 13J shows expression percentage results for tests of Chip type 3 at various pressures (45, 60, 75, 90, and 105 PSI), in various orientations, and using blood from three different donors (A, B, and C).

FIG. 13K shows efficacy results for tests of Chip type 3 at various pressures (45, 60, 75, 90, and 105 PSI) and in various orientations.

FIGS. 13L-13O show FACS plots for tests of chip type 3. GFP fluorescence in cells is plotted against dextran fluorescence in cells.

EMBODIMENTS

Below is an enumerated listing of certain embodiments. In some embodiments, any one or more of the features of any one or more of the embodiments below may be combined with any one or more of the other embodiments, even if the dependencies of the embodiments do not explicitly indicate that the embodiments may be combined.

1. A microfluidic chip for causing the delivery of a payload to a cell, the chip comprising:
   a fluid inlet configured to receive flow of a cell suspension and pass the cell suspension to a first fluid flow region within the microfluidic chip;
   a plurality of constrictions fluidly connected to the first fluid flow region to allow the cell suspension to flow through one or more of the plurality of constrictions from the first fluid flow region to a second fluid flow region within the microfluidic chip, wherein:
     a cross-sectional width of each of the plurality of constrictions is less than a diameter of cells in the cell suspension, such that membranes of the cells are perturbed when passing through the constrictions such that a payload is able to pass through the perturbed cell membranes; and
     a quotient of a cross-sectional area over a cross-sectional perimeter of each of the plurality of constrictions is greater than greater than or equal to 0.5 μm; and
   a fluid outlet configured to allow the cell suspension to flow from the second fluid flow region out of the microfluidic chip.

2. The microfluidic chip of embodiment 1, wherein a cross-sectional width of each of the plurality of constrictions is less than or equal to one or more of the following: 1.8 μm, 1.9 μm, 2 μm, 3 μm, 4 μm, 5 μm, 6 μm, or 10 μm.

3. The microfluidic chip of any one of embodiments 1-2, wherein a cross-sectional height of each of the plurality of constrictions is greater than or equal to 20 μm.

4. The microfluidic chip of embodiment 3, wherein each of the constrictions are formed by etching into a substrate of the microfluidic chip, wherein the cross-sectional height of each of the plurality of constrictions is defined by an etch depth of the etching.

5. The microfluidic chip of embodiment 4, wherein the substrate comprises silicon.

6. The microfluidic chip of any one of embodiments 4-5, wherein the etching comprises deep reactive ion etching.

7. The microfluidic chip of any one of embodiments 1-6, wherein the plurality of constrictions includes greater than 1000 constrictions.

8. The microfluidic chip of any of embodiments 1-7, wherein the plurality of constrictions are positioned in parallel to one another to form a boundary between the first fluid flow region and the second fluid flow region.

9. The microfluidic chip of embodiment 8, wherein a ratio of a distance from the inlet port to a nearest point on the boundary to a length of the boundary is greater than or equal to 0.5.

10. The microfluidic chip of any one of embodiments 8-9, wherein a ratio of a distance to farthest point on the boundary from the inlet port to a distance to a nearest point of the boundary from the inlet port is less than or equal to 1.5.

11. The microfluidic chip of any one of embodiments 8-10, wherein the boundary comprises a portion extending in a linear manner.

12. The microfluidic chip of any one or embodiments 8-11, wherein a length of the boundary is greater than or equal to 4 mm.

13. The microfluidic chip of any one of embodiments 1-12, wherein the microfluidic chip is configured to operate at an overall throughput rate of greater than or equal to 1 mL/min across all constrictions.

14. The microfluidic chip of any of embodiments 1-13, wherein the microfluidic chip is configured to operate at a pressure of greater than or equal to 10 psi.

15. The microfluidic chip of any of embodiments 1-14, wherein each of the plurality of constrictions is positioned adjacent to a respective approach region comprising a tapering wall that tapers toward the constriction.

16. The microfluidic chip of embodiment 15, wherein the tapering wall tapers toward the constriction at an angle of greater than or equal to 10 degrees and less than or equal to 80 degrees from a side wall of the constriction.

17. The microfluidic chip of any of embodiments 1-16, wherein the microfluidic chip is configured such that an average per-constriction volumetric flow rate for the plurality of constrictions is greater than or equal to 1 µL/min.

18. The microfluidic chip of any one of embodiments 1-17, comprising one or more pillars intersecting the first fluid flow region and connecting a plane of a first inner surface of the first fluid flow region to a plane of a second inner surface of the first fluid flow region.

19. The microfluidic chip of any one of embodiments 1-18, wherein a ratio of an overall etched area forming the first fluid flow region and the second fluid flow region is less than or equal to 50% of a surface area of the microfluidic chip.

20. A method of causing delivery of a payload to a cell, the method comprising:
receiving flow of a cell suspension into a first fluid flow region of a microfluidic chip, the cell suspension comprising a plurality of cells; and
causing the cell suspension to flow from the first fluid flow region through a plurality of constrictions of the microfluidic chip, wherein:
a cross-sectional width of each of the plurality of constrictions is less than a diameter of cells in the cell suspension, such that membranes of the cells are deformed when passing through the constrictions such that a payload is able to pass through the deformed cell membranes; and
a quotient of a cross-sectional area over a cross-sectional perimeter of each of the plurality of constrictions is greater than greater than or equal to 0.5 µm.

21. The method of embodiment 20, wherein the cell suspension comprises the payload.

22. The method of any of embodiments 20-21, comprising causing the payload to come into contact with the cell suspension following perturbation of the cell membranes.

23. The method of embodiment 22, wherein a percentage of cells to which the payload is delivered following causing the payload to come into contact with the cell suspension is greater than or equal to 30%.

24. The method of any of embodiments 20-23, wherein a percentage of viable cells in the cell suspension following passage of the cell suspension through the plurality of constrictions of the microfluidic chip is greater than or equal to 30%.

25. The method of any of embodiments 20-24, wherein a cross-sectional width of each of the plurality of constrictions is less than or equal to one or more of the following: 1.8 µm, 1.9 µm, 2 µm, 3 µm, 4 µm, 5 µm, 6 µm, or 10 µm.

26. The method of any one of embodiments 20-25, wherein a cross-sectional height of each of the plurality of constrictions is greater than or equal to 20 µm.

27. The method of any one of embodiments 20-26, wherein the plurality of constrictions includes greater than 1000 constrictions.

28. The method of any one of embodiments 20-27, wherein the microfluidic chip is configured to operate at an overall throughput rate of greater than or equal to 1 mL/min across all constrictions.

29. The method of any of embodiments 20-28, wherein causing the cell suspension to flow from the first fluid flow region through the plurality of constrictions comprises forcing flow of the fluid at a pressure of greater than or equal to 10 psi.

30. The method of any of embodiments 20-29, wherein causing the cell suspension to flow from the first fluid flow region through the plurality of constrictions comprises causing the cell suspension to flow at an average per-constriction volumetric flow rate for the plurality of constrictions of greater than or equal to 1 µL/min.

31. A method of fabricating a microfluidic chip for causing the delivery of a payload to cells, the method comprising:
etching into a substrate to form a first fluid flow region configured to allow a cell suspension to flow from an inlet port through the first fluid flow region; and
etching into the substrate to form a plurality of constrictions configured to allow flow of the cell suspension from the first fluid flow region through the constrictions, wherein:
a cross-sectional width of each of the plurality of constrictions is less than a diameter of cells in the cell suspension, such that membranes of the cells are deformed when passing through the constrictions such that a payload is able to pass through the deformed cell membranes; and
a quotient of a cross-sectional area over a cross-sectional perimeter of each of the plurality of constrictions is greater than greater than or equal to 0.5 µm.

32. The method of embodiment 31, comprising affixing a cover layer to the etched substrate to enclose the first fluid flow region and the plurality of constrictions.

33. The method of any one of embodiments 31-32, wherein etching into the substrate to form the plurality of constrictions comprises deep reactive ion etching.

34. The method of any one of embodiments 31-33, wherein etching into the substrate to form the plurality of constrictions comprises etching to a depth of greater than or equal to 50 µm.

35. The method of any one of embodiments 31-34, comprising depositing a layer of material onto the substrate following etching into the substrate, wherein depositing the layer causes decreasing the widths of the plurality of constrictions.

36. A microfluidic chip for causing the delivery of a payload to a cell, the chip comprising:
a fluid inlet configured to receive flow of a cell suspension and pass the cell suspension to a first fluid flow region within the microfluidic chip;
a first plurality of constrictions fluidly connected to the first fluid flow region to allow the cell suspension to flow through one or more of the first plurality of constrictions from the first fluid flow region to a second fluid flow region within the microfluidic chip; and
a second plurality of constrictions fluidly connected to the second fluid flow region to allow the cell suspension to flow through one or more of the second plurality of constrictions from the second fluid flow region to a third fluid flow region within the microfluidic chip, wherein:
a cross-sectional width of each of the constrictions of the first plurality of constrictions and the second plurality of constrictions is less than a diameter of cells in the cell suspension, such that membranes of the cells are perturbed when passing through the constrictions such that a payload is able to pass through the perturbed cell membranes; and
a quotient of a cross-sectional area over a cross-sectional perimeter of each of the constrictions of the first plurality of constrictions and the second plurality of constrictions is greater than greater than or equal to 0.5 µm.

37. The microfluidic chip of embodiment 36, wherein a cross-sectional width of each of the first plurality of constrictions and the second plurality of constrictions is less than or equal to one or more of the following: 1.8 µm, 1.9 µm, 2 µm, 3 µm, 4 µm, 5 µm, 6 µm, or 10 µm.

38. The microfluidic chip of any one of embodiments 36-37, wherein a cross-sectional height of each of the first plurality of constrictions and the second plurality of constrictions is greater than or equal to 20 µm.

39. The microfluidic chip of embodiment 38, wherein each of the first plurality of constrictions and the second plurality of constrictions are formed by etching into a substrate of the microfluidic chip, wherein the cross-sectional height of each of the plurality of constrictions is defined by an etch depth of the etching.

40. The microfluidic chip of any one of embodiments 36-39, wherein the first plurality of constrictions and the second plurality of constrictions each includes greater than 1000 constrictions.

41. The microfluidic chip of any one of embodiments 36-40, wherein the first plurality of constrictions and the second plurality of constrictions are separated from one another by a closest spacing distance of greater than or equal to 25 µm.

42. The microfluidic chip of any one of embodiments 36-41, wherein the microfluidic chip is configured to operate at an overall throughput rate of greater than or equal to 1 mL/min across all constrictions.

43. The microfluidic chip of any of embodiments 36-42, wherein the microfluidic chip is configured to operate at a pressure of greater than or equal to 10 psi.

44. The microfluidic chip of any of embodiments 36-43, wherein the microfluidic chip is configured such that an average per-constriction volumetric flow rate for the first plurality of constrictions and the second plurality of constrictions is greater than or equal to 1 µL/min.

What is claimed is:

1. A microfluidic chip for causing the delivery of a payload to a cell, the chip comprising:
a fluid inlet port configured to receive flow of a cell suspension and pass the cell suspension to a first fluid flow region within the microfluidic chip;
a plurality of constrictions fluidly connected to the first fluid flow region to allow the cell suspension to flow through one or more of the plurality of constrictions from the first fluid flow region to a second fluid flow region within the microfluidic chip, wherein:
a cross-sectional width of each of the plurality of constrictions is less than a diameter of cells in the cell suspension, such that membranes of the cells are perturbed when passing through the plurality of constrictions such that a payload is able to pass through the perturbed cell membranes; and
a quotient of a cross-sectional area over a cross-sectional perimeter of each of the plurality of constrictions is greater than greater than or equal to 0.5 µm;
one or more pillars intersecting the first fluid flow region and connecting a plane of a first inner surface of the first fluid flow region to a plane of a second inner surface of the first fluid flow region; and
a fluid outlet configured to allow the cell suspension to flow from the second fluid flow region out of the microfluidic chip.

2. The microfluidic chip of claim 1, wherein a cross-sectional width of each of the plurality of constrictions is less than or equal to one or more of the following: 1.8 µm, 1.9 µm, 2 µm, 3 µm, 4 µm, 5 µm, 6 µm, or 10 µm.

3. The microfluidic chip of claim 1, wherein a cross-sectional height of each of the plurality of constrictions is greater than or equal to 20 µm.

4. The microfluidic chip of claim 3, wherein each of the plurality of constrictions are formed by etching into a substrate of the microfluidic chip, wherein the cross-sectional height of each of the plurality of constrictions is defined by an etch depth of the etching.

5. The microfluidic chip of claim 4, wherein the substrate comprises silicon.

6. The microfluidic chip of claim 4, wherein the etching comprises deep reactive ion etching.

7. The microfluidic chip of claim 1, wherein the plurality of constrictions includes greater than 1000 constrictions.

8. The microfluidic chip of claim 1, wherein the plurality of constrictions are positioned in parallel to one another to form a boundary between the first fluid flow region and the second fluid flow region.

9. The microfluidic chip of claim 8, wherein a ratio of a distance from the fluid inlet port to a nearest point on the boundary to a length of the boundary is greater than or equal to 0.5.

10. The microfluidic chip of claim 8, wherein a ratio of a distance to farthest point on the boundary from the fluid inlet port to a distance to a nearest point of the boundary from the inlet port is less than or equal to 1.5.

11. The microfluidic chip of claim 8, wherein the boundary comprises a portion extending in a linear manner.

12. The microfluidic chip of claim 8, wherein a length of the boundary is greater than or equal to 4 mm.

13. The microfluidic chip of claim 1, wherein the microfluidic chip is configured to operate at an overall throughput rate of greater than or equal to 1 mL/min across all constrictions.

14. The microfluidic chip of claim 1, wherein the microfluidic chip is configured to operate at a pressure of greater than or equal to 10 psi.

15. The microfluidic chip of claim 1, wherein each of the plurality of constrictions is positioned adjacent to a respective approach region comprising a tapering wall that tapers toward the constriction.

16. The microfluidic chip of claim 15, wherein the tapering wall tapers toward the constriction at an angle of greater than or equal to 10 degrees and less than or equal to 80 degrees from a side wall of the constriction.

17. The microfluidic chip of claim 1, wherein the microfluidic chip is configured such that an average per-constriction volumetric flow rate for the plurality of constrictions is greater than or equal to 1 µL/min.

18. The microfluidic chip of claim 1, wherein a ratio of an overall etched area forming the first fluid flow region and the second fluid flow region is less than or equal to 50% of a surface area of the microfluidic chip.

19. A microfluidic chip for causing the delivery of a payload to a cell, the chip comprising:
a fluid inlet configured to receive flow of a cell suspension and pass the cell suspension to a first fluid flow region within the microfluidic chip;
a first plurality of constrictions fluidly connected to the first fluid flow region to allow the cell suspension to flow through one or more of the first plurality of constrictions from the first fluid flow region to a second fluid flow region within the microfluidic chip; and
a second plurality of constrictions fluidly connected to the second fluid flow region to allow the cell suspension to flow through one or more of the second plurality of constrictions from the second fluid flow region to a third fluid flow region within the microfluidic chip, wherein:
a cross-sectional width of each of the constrictions of the first plurality of constrictions and the second plurality of constrictions is less than a diameter of cells in the cell suspension, such that membranes of the cells are perturbed when passing through the constrictions such that a payload is able to pass through the perturbed cell membranes; and
a quotient of a cross-sectional area over a cross-sectional perimeter of each of the constrictions of the first plurality of constrictions and the second plurality of constrictions is greater than greater than or equal to 0.5 μm.

20. The microfluidic chip of claim 19, wherein a cross-sectional width of each of the first plurality of constrictions and the second plurality of constrictions is less than or equal to one or more of the following: 1.8 μm, 1.9 μm, 2 μm, 3 μm, 4 μm, 5 μm, 6 μm, or 10 μm.

21. The microfluidic chip of claim 19, wherein a cross-sectional height of each of the first plurality of constrictions and the second plurality of constrictions is greater than or equal to 20 μm.

22. The microfluidic chip of claim 21, wherein each of the first plurality of constrictions and the second plurality of constrictions are formed by etching into a substrate of the microfluidic chip, wherein the cross-sectional height of each of the plurality of constrictions is defined by an etch depth of the etching.

23. The microfluidic chip of claim 19, wherein the first plurality of constrictions and the second plurality of constrictions each includes greater than 1000 constrictions.

24. The microfluidic chip of claim 19, wherein the first plurality of constrictions and the second plurality of constrictions are separated from one another by a closest spacing distance of greater than or equal to 25 μm.

25. The microfluidic chip of claim 19, wherein the microfluidic chip is configured to operate at an overall throughput rate of greater than or equal to 1 mL/min across all constrictions.

26. The microfluidic chip of claim 19, wherein the microfluidic chip is configured to operate at a pressure of greater than or equal to 10 psi.

27. The microfluidic chip of claim 19, wherein the microfluidic chip is configured such that an average per-constriction volumetric flow rate for the first plurality of constrictions and the second plurality of constrictions is greater than or equal to 1 μL/min.

* * * * *